United States Patent
Perfettini et al.

(10) Patent No.: US 11,517,575 B2
(45) Date of Patent: *Dec. 6, 2022

(54) USE OF MINAPRINE TO REDUCE TUMOR GROWTH

(71) Applicant: Institut Gustave-Roussy, Villejuif (FR)

(72) Inventors: Jean Luc Perfettini, Meaux (FR); Eric Deutsch, Paris (FR); Catherine Brenner, Le Chesnay (FR); Jean-Christophe Cintrat, Igny (FR); Frederic Taran, Gif sur Yvette (FR)

(73) Assignee: Institut Gustave Roussy, Villejuif (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/963,338

(22) PCT Filed: Jan. 23, 2019

(86) PCT No.: PCT/EP2019/051637
§ 371 (c)(1),
(2) Date: Jul. 20, 2020

(87) PCT Pub. No.: WO2019/145363
PCT Pub. Date: Aug. 1, 2019

(65) Prior Publication Data
US 2021/0060029 A1    Mar. 4, 2021

(30) Foreign Application Priority Data

Jan. 23, 2019 (WO) ................ PCT/EP2019/051637

(51) Int. Cl.
| | | |
|---|---|---|
| *A61K 31/5377* | (2006.01) | |
| *A61K 31/15* | (2006.01) | |
| *A61K 31/4166* | (2006.01) | |
| *A61K 31/513* | (2006.01) | |
| *A61N 5/10* | (2006.01) | |
| *G01N 33/50* | (2006.01) | |
| *A61P 35/00* | (2006.01) | |
| *A61K 9/00* | (2006.01) | |

(52) U.S. Cl.
CPC ........ *A61K 31/5377* (2013.01); *A61K 9/0019* (2013.01); *A61K 31/15* (2013.01); *A61K 31/4166* (2013.01); *A61K 31/513* (2013.01); *A61N 5/10* (2013.01); *A61P 35/00* (2018.01); *G01N 33/5011* (2013.01); *A61N 2005/1098* (2013.01); *G01N 2510/00* (2013.01)

(58) Field of Classification Search
CPC .................................................. A61K 31/5377
See application file for complete search history.

(56) References Cited

U.S. PATENT DOCUMENTS

2005/0112059 A1   5/2005  Newman et al.
2015/0185202 A1   7/2015  Perfettini et al.

FOREIGN PATENT DOCUMENTS

WO   WO 2012/018761 A2 *  2/2012   ............ A61K 31/39
WO       2018134443 A1     7/2018

OTHER PUBLICATIONS

Wermuth, Med. Chem. Commun., (2011), 2, pp. 935-941.*
Biziere et al., "Pharmacological evaluation of minaprine dihydrochloride, a new psychotropic drug," Database accession No. NLM6890359, Nov. 2014.
International Search Report and Written Opinion issued in application No. PCT/EP2019/051637 dated Feb. 20, 2019.
Wardman, "Chemical Radiosensitzers for Use in Radiotherapy," Clinical Oncology, vol. 19, No. 6, pp. 397-417, May 2007.
Yamamoto et al., "Bafilomycin A1 Prevents Maturation of Autophagic Vacuoles by Inhibiting Fusion between Autophagosomes and Lyosomes in Rat Hepatoma Cell Line, H-4-II-E Cells," Cell Structure and Function, vol. 23, pp. 35-42, 1998.
Zhang et al., "Caspase independence of radio-induced cell death," Oncogene, vol. 25, pp. 7758-7770, Jul. 2006.
Zhang et al., "Robust statistical methods for hit selection in RNA interference high-throughput screening experiments," Pharmacogenics, vol. 7, No. 3, pp. 299-309, 2006.
Aaes et al., "Vaccination with Necroptotic Cancer Cells Induces Efficient Anti-tumor Immunity," Cell Reports, vol. 15, pp. 274-287, Apr. 2016.
Abend et al., "Reasons to consider the significance of apoptosis for cancer therapy," Int. J. Radiat. Biol., vol. 79, No. 12, pp. 927-941, Dec. 2003.
Apetoh et al., "The interaction between HMGB1 and TLR4 dictates the outcome of anticancer chemotherapy and radiotherapy," Immunological Reviews, vol. 220, pp. 47-59, 2007.
Apetoh et al., "Toll-like receptor 4-dependent contribution of the immune system to anticancer chemotherapy and radiotherapy," Nature Medicine, vol. 13, No. 9, pp. 1050-1059, Sep. 2007.
Bartosh et al., "Cancer cells enter dormancy after cannibalizing mesenchymal stem/stromal cells (MSCs)," PNAS, vol. 113, pp. E6447-E6456, Oct. 2016.
Benseler et al., "Hepatocyte entry leads to degradation of autoreactive CD8 T cells," PNAS, vol. 108, No. 40, pp. 16735-16740, Oct. 2011.
Brown et al., "Eaten alive! Cell Death by primary phagocytosis: 'phagoptosis'," Trends in Biochemical Sciences, vol. 37, No. 8, pp. 325-332, Aug. 2012.
Brown et al., "Phagoptosis—Cell Death by Phagocytosis—Plays Central Roles in Physiology, Host Defense and Pathology," Current Molecular Medicine, vol. 15, pp. 1-10, 2015.
Cano et al., "Homotypic cell cannibalism, a cell-death process regulated by the nuclear protein 1, opposes to metastasis in pancreatic cancer," EMBO Molecular Medicine, vol. 4, pp. 964-979, 2012.

(Continued)

Primary Examiner — Brian J Davis
(74) Attorney, Agent, or Firm — Rouget F. Henschel; Potomac Law Group, PLLC

(57) ABSTRACT

The present invention is drawn to the use of Minaprine dihydrochloride and analogs thereof, for reducing tumor growth when administered to a patient suffering from cancer.

7 Claims, 17 Drawing Sheets

(56) References Cited

OTHER PUBLICATIONS

Figure 1:
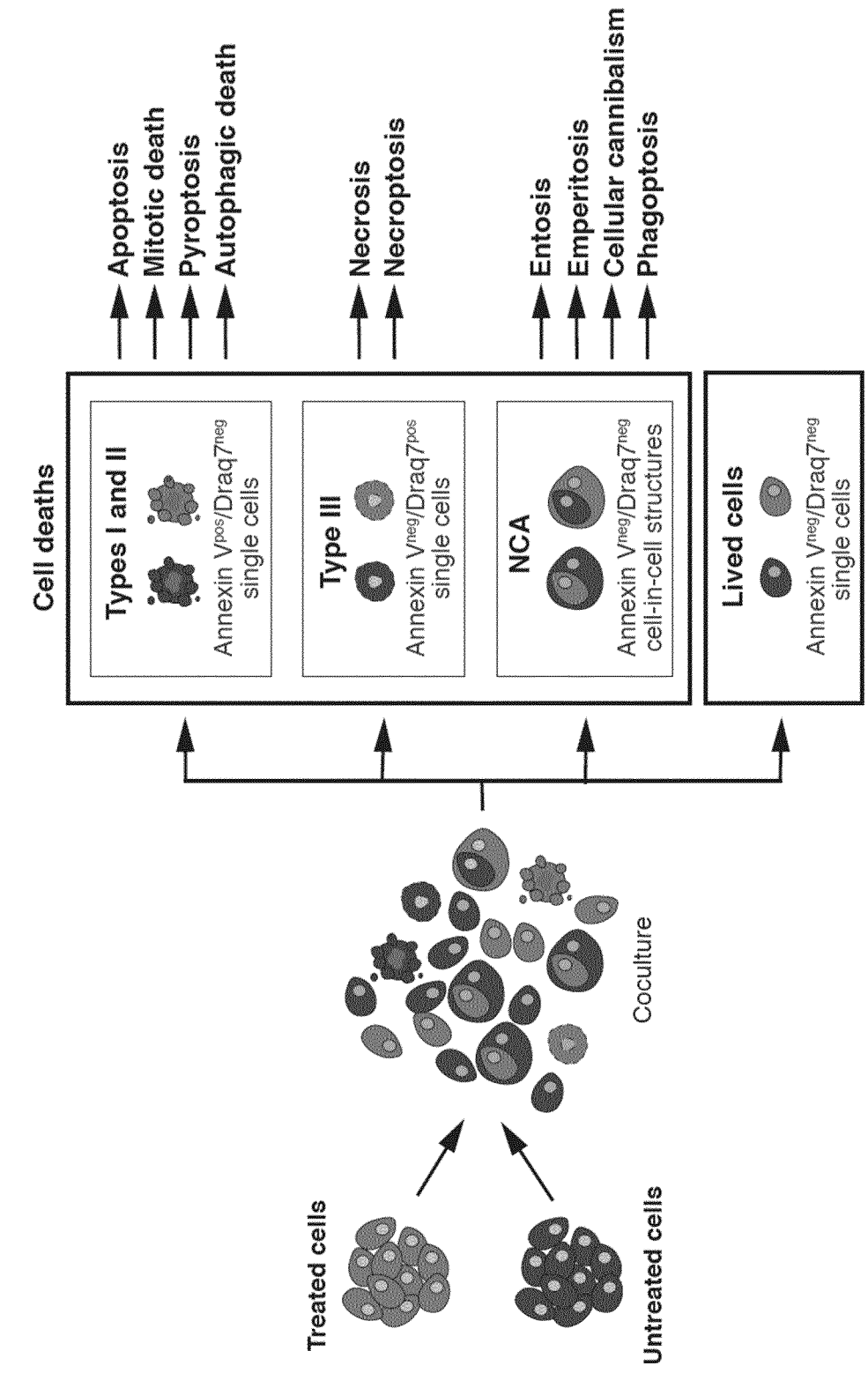
Figure 1:
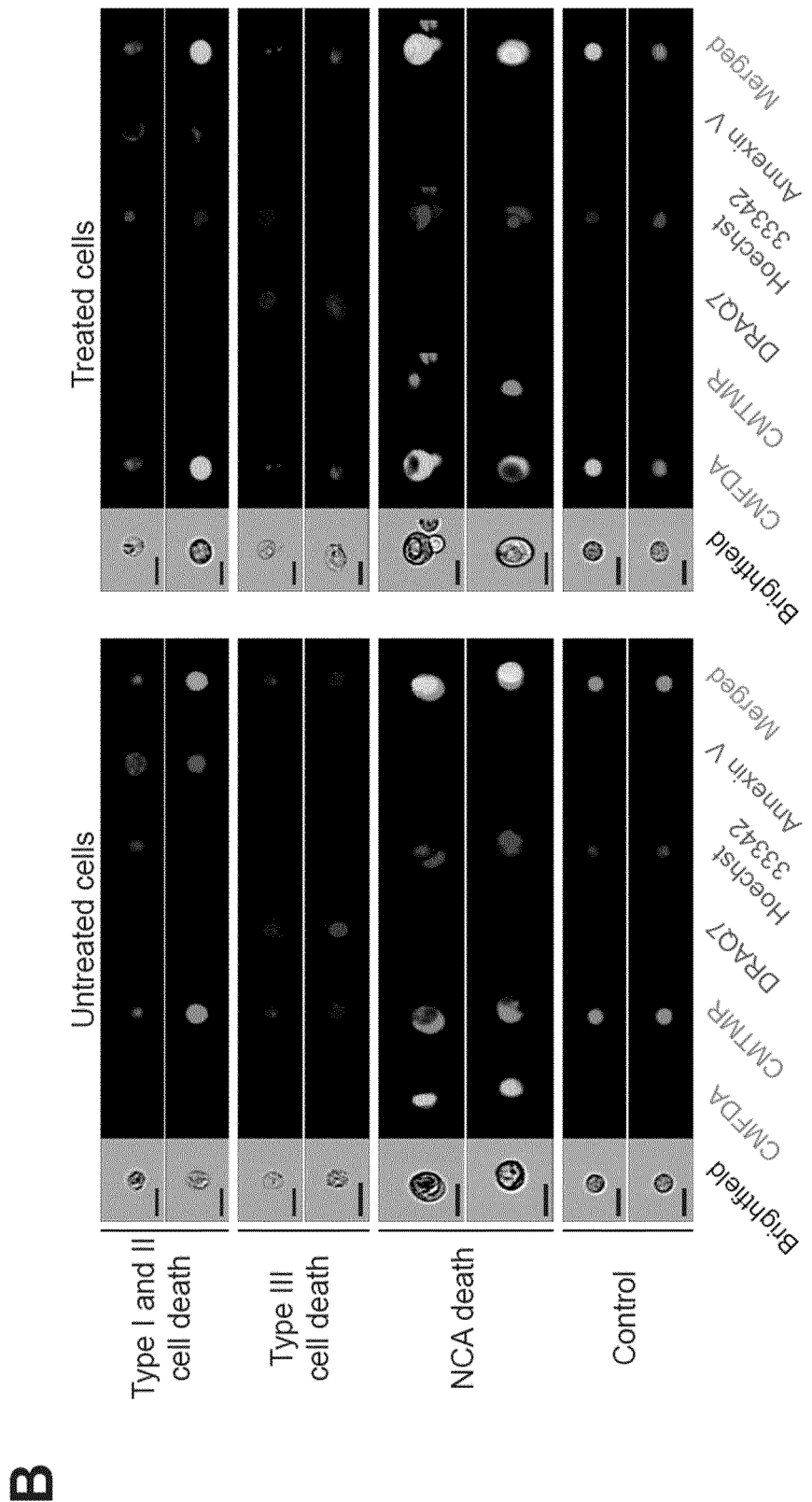

Casares et al., "Caspase-dependent immunogenicity of doxorubicin-induced tumor cell death," The Journal of Experimental Medicine, vol. 202, No. 12, pp. 1691-1701, Dec. 2005.
Castedo et al., "Cell death by mitotic catastrophe: a molecular definition," Oncogene, vol. 23, pp. 2825-2837 2004.
Castedo et al., "The cell cycle checkpoint kinase Chk2 is a negative regulator of mitotic catastrophe," Oncogene, vol. 23, pp. 4353-4361, 2004.
Degterev et al., "Chemical inhibitor of nonapoptotic cell death with therapeutic potential ischemic brain injury," Nature Chemical Biology, vol. 1, No. 2, pp. 112-119, Jul. 2005.
Demaria et al., "Ionizing Radiation Inhibition of Distant Untreated Tumors (Abscopal Effect) is Immune Mediated," Int. J. Radiation Oncology Biol. Phys., vol. 58, No. 3, pp. 862-870, 2004.
Dewan et al., "Fractionated but not single dose radiotherapy induces an immune-mediated abscopal effect when combined with anti-CTLA-4 antibody," Clin. Cancer Res., vol. 15, No. 17, pp. 5379-5388, Sep. 2009.
Garcia-Calvo et al., "Inhibition of Human Caspases by Peptide-based and Macromolecular Inhibitors," The Journal of Biological Chemistry, vol. 273, No. 49, pp. 32608-32613, 1998.
Ghiringhelli et al., "Activation of the NLRP3 inflammasome in dendritic cells induces IL-1beta-dependent adaptive immunity against tumors," Nature Medicine, vol. 15, No. 10, pp. 1170-1178, Oct. 2009.
Green et al., "Immunogenic and Tolergenic Cell Death," Nat. Rev. Immunol., vol. 9, No. 5, p. 353, May 2009.
Gudkov et al., "The Role of p53 in Determining Sensitivity to Radiotherapy," Nature Reviews Cancer, vol. 3, pp. 117-128, Feb. 2003.
He et al., "Modeling cell-in-cell structure into its biological significance," Cell Death and Disease, vol. 4, p. e630, May 2013.
Kershaw et al., "Enhancing immunotherapy using chemotherapy and radiation to modify the tumor microenvironment," Oncoimmunology, vol. 2, No. 9, p. e25962, Sep. 2013.
Khandelwal et al., "Reduced expression of CD47 during murine red blood cell (RBC) senescence and its role in RBC clearance from the circulation," Hematopoiesis, vol. 47, pp. 1725-1732, Sep. 2007.
Kingsley, "An interesting case of possible abscopal effect in malignant melanoma," British Journal of Radiology, vol. 48, pp. 863-866, Oct. 1975.
Kroemer et al., "Classification of Cell Death: recommendations of the Nomenclature Committee on Cell Death 2009," Cell Death Differ., vol. 16, No. 1, pp. 3-11, Jan. 2009.
Lagasse et al., "bcl-2 Inhibits Apoptosis of Neutrophils but Not Their Engulfment by Macrophages," J. Exp. Med., vol. 179, pp. 1047-1052, Mar. 1994.
Li et al., "Entosis Allows Timely Elimination of the Luminal Epithelial Barrier for Embryo Implantation," Cell Reports, vol. 11, No. 3, pp. 358-365, Apr. 2015.
Lowe et al., "p53 is required for radiation-induced apoptosis in mouse thymocytes," Nature, vol. 362, pp. 847-849, Apr. 1993.
Lugini et al., "Cannibalism of Live Lymphocytes by Human Metastatic but Not Primary Melanoma Cells," Cancer Res., vol. 66, No. 7, pp. 3629-3638, Apr. 2006.
Meijer et al., "Biochemical and cellular effects of roscovitine, a potent and selective inhibitor of the cyclin-dependent kinases cdc2, cdk2, and cdk5," Eur. J. Biochem., vol. 243, pp. 527-536, 1997.
Meng et al., "Blockade of Tumor Necrosis Factor alpha Signaling in Tumor-Associated Macrophages as a Radiosensitizing Strategy," Cancer Research, vol. 70, No. 4, pp. 1534-1543, Feb. 2010.
Menger et al., "Cardiac Glycosides Exert Anticancer Effects by Inducing Immunogenic Cell Death," Science Translational Medicine, vol. 4, Issue 143, 4:143ra199, 2012.
Miao et al., "Caspase-1-induced pyroptosis is an innate immune effector mechanism against intracellular bacteria," Nat. Immunol., vol. 11, No. 12, pp. 1136-1142, Dec. 2010.
Michaud et al., "Autophagy-Dependent Anticancer Immune Responses Induced by Chemotherapeutic Agents in Mice," Science, vol. 334, pp. 1573-1577, Dec. 2011.
Ni et al., "Implication of cell-in-cell structures in the transmission of HIV to epithelial cells," Cell Research, vol. 25, pp. 1265-1268, Oct. 2015.
Ni et al., "In-cell infection: a novel pathway for Epstein-Barr virus infection mediated by cell-in-cell structures," Cell Research, vol. 25, pp. 785-800, Apr. 2015.
Obeid et al., "Calreticulin exposure dictates the immunogenicity of cancer cell death," Nature Medicine, vol. 13, No. 1, pp. 54-61, Jan. 2007.
Obeid et al., "Calreticulin exposure is required for the immunogenicity of y-irradiation and UVC light-induced apoptosis," Cell Death and Differentiation, vol. 14, pp. 1848-1850, 2007.
Ohba et al., "Abscopal regression of hepatocellular carcinoma after radiotherapy for bone metastasis," Gut, vol. 43, pp. 575-577, 1998.
Overholtzer et al., "A Nonapoptotic Cell Death Process, Entosis, that Occurs by Cell-in-Cell Invasion," Cell, vol. 131, pp. 966-979, Nov. 2007.
Overholtzer et al., "The cell biology of cell-in-cell structures," Molecular Cell Biology, vol. 9, pp. 796-809, Oct. 2008.
Postow et al., "Immunologic Correlates of the Abscopal Effect in a Patient with Melanoma," N. Engl. J. Med., vol. 366, No. 10, pp. 925-931, Mar. 2012.
Rees et al., "Abscopal regression following radiotherapy for adenocarcinoma," British Journal of Radiology, vol. 56, pp. 63-66, Jan. 1983.
Sierro et al., "Suicidal Emperipolesis: A Process Leading to Cell-in-Cell Structures, T Cell Clearance and Immune Homeostasis," Current Molecular Medicine, vol. 15, pp. 1-9, 2015.
Sun et al., "Competition between human cells by entosis," Cell Research, vol. 24, pp. 1299-1310, Oct. 2014.
Sun et al., "Induction of entosis by epithelial cadherin expression," Cell Research, vol. 24, pp. 1288-1298, Oct. 2014.
Tobias, "Clinical practice of radiotherapy," The Lancet, vol. 339, pp. 159-163, Jan. 1992.
Vakifahmetoglu et al., "Death through a tragedy: mitotic catastrophe," Cell Death and Differentiation, vol. 15, pp. 1153-1162, 2008.
Vanden Berghe et al., "Necroptosis, necrosis and secondary necrosis converge on similar cellular disintegration features," Cell Death and Differentiation, vol. 17, pp. 922-930, Dec. 2009.
Wang et al., "Internalization of NK cells into tumor cells requires ezrin and leads to programmed cell-in-cell death," Cell Research, vol. 19, pp. 1350-1362, Sep. 2009.
Wang et al., "Rapid reuptake of granzyme B leads to emperiotosis: an apoptotic cell-in-cell death of immune killer cells inside tumor cells," Cell Death and Disease, vol. 4, p. e856, 2013.
Kan et al., "Effect of the Antidepressant Minaprine on Both Forms of Monoamie Oxidase in the Rat," Biochemical Pharmacology, vol. 35, No. 6, pp. 973-978, 1986.
Youdim et al., "The therapeutic potential of monamine oxidase inhibtors," Nature Reviews, vol. 7, pp. 295-309, Apr. 2006.
Brieger et al., "The Cyclooxygenase Inhibitor Flurbiprofen Reduces Radiation-Induced Angiogenic Growth Factor Secretion of Squamous Cell Carcinoma Cell Lines", N. Y. Academy of Science, 1030, p. 37-42, 2004.
Edwards et al., "Double-blind comparative study of the antidepressant, unwanted and cardiac effects of minaprine and amitriptyline", Blackwell Science Ltd, vol. 42, p. 491-498, 1996.
Ferretti et al., "Biochemical effects of minaprine on striatal dopaminergic neurons in rats," J. Pharm.Pharmacol., vol. 36, No. 1, pp. 48-50, Jan. 1984, Abstract.
Finberg et al., "Inhibitors of MAO-A and MAO-B in Psychiatry and Neurology," Frontiers in Pharmacology, vol. 7, Article 340, Oct. 2016.
Fong et al., "Quantitative analysis of minaprine and some of its metabolites with application to kinetic studies in rats," J. Chromatogr., vol. 259, No. 1, p. 259, Mar. 1983, Abstract.
Haux et al., Digitoxin sensitizes malignant breast cancer cells for radiation in vitro, Journal. of Oncology, vol. 31, No. 3, p. 61-65, 1999.

(56) References Cited

OTHER PUBLICATIONS

Hong et al., "Discovery of monoamine oxidase inhibitors by medicinal chemistry approaches," Med. Chem. Commun., vol. 10, pp. 10-25, 2019.

Isel et al . . . , "Alterations of serotonin neurotransmission and inhibition of mouse-killing behavior: III. Effects of minaprine, CM 30366 and SR 95191," Pharmacol. Biochem. Behav., vol. 33, No. 3, pp. 655-662, Jul. 1989, Abstract.

Kang et al.,"Lanatoside C suppressed colorectal cancer cell growth by inducing mitochondrial dysfunction and increased radiation sensitivity by impairing DNA damage repair",Oncotarget, vol. 7, No. 5, p. 6074-6087, Feb. 2, 2016.

Meyer, "A concise guide to monoamine oxidase inhibitors," Current Psychiatry, vol. 16, No. 12, pp. 15-23, Dec. 2017.

Norman et al., "New pharmacological approaches to the management of depression: from theory to clinical practice," Aust. NZ J. Psychiatry, vol. 26, No. 1, pp. 73-81, Mar. 1992, Abstract.

Okumura , "Relation Between the Biological Action of Radiations and Purine Metabolism", The SHOWA University Journal of Medicalsciences, vol. 27, No. 8, p. 643-654, Aug. 28, 1967.

Puglisi-Allegra et al., "Post-training minaprine enhances memory storage in mice: involvement of DI and D2 dopamine receptors," Psychopharmacology, vol. 113, No. 3-4, pp. 476-480, Jan. 1994, Abstract.

Ramsay et al., "Assessment of Enzyme Inhibition: A Review with Examples from the Development of Monoamine Oxidase and Cholinesterase Inhibitory Drugs," Molecules, vol. 22, p. 1192, Jul. 2017.

Riederer et al., "MAO-inhibitors in Parkinson's Disease," Experimental Neurobioiogy, vol. 20, pp. 1-17, Mar. 2011.

Thomas et al., "combination Therapy with Monoamine Oxidase Inhibitors and Other Antidepressants or Stimulants: Strategies for the Management of Treatment-Resistant Depression," Pharmacotherapy, vol. 35, No. 4, pp. 433-449, 2015.

Warter et al., "Immediate effects of 14 non MAOI antidepressants in rats with spontaneous petit mal-iike seizures," Prog. Neuropsychoparmacol. Biol. Psychiatry, vol. 14, No. 2, pp. 261-270, 1990, Abstract.

Zeynep et al., "Syntheses and In Vitro Anticancer Properties of Novel Radiosensitizers", Chem Biol Drug Des, vol. 80, p. 853-861, Apr. 2, 2012.

Zhang et al., "Enhancement of recombinant myricetin on the radiosensitivity of lung cancer A549 and H1299 cells", BioMed Central, Diagnostic Pathology 9:68, 2014.

\* cited by examiner

USE OF MINAPRINE TO REDUCE TUMOR GROWTH

SUMMARY

The present invention is drawn to the use of Minaprine dihydrochloride and analogs thereof, for reducing tumor growth when administered to a patient suffering from cancer.

BACKGROUND OF THE INVENTION

Radiotherapy is one of the most common anti-tumor strategies used in cancer treatments. More than half of patients with cancers are treated with radiotherapy. The use of radiotherapy (alone or in combination with surgery and chemotherapy) is central to the management of tumors of head and neck, breast, lung, prostate, digestive and cervical cancer[1]. Exposure to ionizing radiation (IR) of tumor tissues triggers various lethal processes such as apoptosis, autophagic cell death, mitotic catastrophe or senescence. These mechanisms contribute to the destruction of cancer cells in the irradiated tissues, but can also induce the immunogenicity of irradiated tumor cells[2, 3], modify the tumor microenvironment and allow the development of an anti-tumor immune response involving the release of danger signals (adenosine triphosphate and HMGB1 protein)[4,5], the activation of purinergic receptors (notably P2X7 and P2Y2)[4], the TLR4 receptor[2, 3] and the NLRP3 inflammasome[4]. The relationship between the local tumor response and the stimulation of the immune system is illustrated by describing a remote effect on non-irradiated cancer cells. This paradoxical effect, also known as the abscopal effect, has been studied for many years in different murine tumor models as well as in patients[6-9]. Its detection correlates positively with the presence of a high amount of proinflammatory cytokines (such as TNF alpha), of interferon (IFN) gamma producing T cells and requires the development of an effective immunological response to be observed[10,11]. This effect is also observed in patients treated with radiotherapy in combination with immuno-modulating agents (such as Ipilimumab or Interleukin-2) th. The description of the abscopal effect reinforces the recent descriptions in many animal models of a major contribution of various components of the immune system to the response to radiotherapy. The central role of immune cells (including tumor-associated macrophages, T lymphoid cells and dendritic cells) has recently been studied and highlighted by the influence of their therapeutic modulation with modulators of immunological checkpoints (such as the use of monoclonal antibodies against CTLA4 or PD1) or macrophage activation (with monoclonal antibodies directed against CSF1R). Despite the central role of radiotherapy in the anti-tumor therapeutic arsenal, the biological processes involved in the elimination of tumor cells are still partially defined and controversial. Early studies on radio-induced tumor cell death are relatively old and occurred before the recent discovery of new cell death processes as well as of the central role of the immune system in the elimination of tumor cells following irradiation.

Scientific and technological advances in recent years revealed the existence of several processes of cell death. A classification of cell death modalities mainly built on morphological and functional criteria has been proposed[13] and subdivided lethal processes into three distinct types: type I cell death (also known as apoptosis), type II cell death (or autophagy) and type III cell death (or necrosis). Initially organized on the apparent distinction between type I and III cell death modalities, between processes that are regulated or accidentally-induced, or by distinguishing cell deaths that are associated with the induction of by-stander inflammatory response in vivo, to lethal processes that were thinking silent or tolerogenic, this classification that still misnamed the type II cell death as autophagy (which is mainly an intracellular survival mechanisms required for the maintenance of cellular homeostasis) did not reflect the aptitude of necrotic deaths to be genetically controlled or immunogenic as revealed by the recent molecular characterization of necroptosis[14,15]. In addition, cell death subroutines that did not or partially reveal these stereotyped morphological, metabolic and biochemical modifications (such as mitotic death and cornification) have been less studied and were grouped in a poorly defined subgroup of cell death modalities, also known as atypical cell death subgroup[13].

In recent years, several new cell death mechanisms (such as entosis or emperitosis) have been described and associated to this neglected subgroup of cell death modalities[16, 17]. The characterization of these atypical death modalities highlighted the existence of cell death processes that are not achieved like typical cell death modalities, in a cell autonomous manner, but are elicited after the engulfment of lived cells by neighbor cells. During decades, non-cell autonomous deaths (NCADs) have been episodically observed and studied. Initially referred as phagoptosis[18, 19] or emperipolesis[20], these processes have been involved in the control of erythrocyte, neutrophil, platelet or T cell homeostasis[18, 21, 22] and thus, proposed as major physiological forms of cell death in the body[18]. Detected as cell-in-cell structures, NCADs have been also observed during ex vivo culture of primary cells[23] or during histological analyses of physiological processes (such as embryo implantation[24] and intrahepatic depletion of autoreactive T cells[25]) or human diseases (including cancer[23], inflammatory syndromes[23], during infectious diseases[26, 27]). Mainly detected after homotypic interactions between malignant cells in human tumors (including breast, cervical and colon carcinomas or melanomas), NCADs are also detected after heterotypic interactions between tumor cells and stroma cells[28], tumor cells and immune effectors (such as lymphocytes[29] and NK cells[30]), but may also be observed after interactions between immune effectors and epithelial cells (as revealed by the destruction of T cells in thymic nurse cells[31] or autoreactive T cells in liver[25]). Recently, NCAD was also associated with infectious diseases. The engulfment of Human immunodeficiency virus 1 (HIV-1) or Epstein barr virus (EBV) infected cells by uninfected cells has been detected during in vitro co-culture and the degradation of internalized infected cells proposed as the first step of a new cell-to-cell mode of viral transmission between infected cells and host cells[26, 27], underlining the ability of NCADs to also contribute to microbial pathogenesis.

The first step of non-cell autonomous death programs starts with the interaction of two cellular partners through membrane adhesion receptors (such as E- or P-cadherins) or stress receptors (such as lipoprotein receptor-related protein) and is followed by the formation of adherent junctions between interacting cells that activates signaling pathways on both interacting cells and may involve small GTPases (such as Rho[32] and Cdc42[33]) and ROCK kinases[16]. Then, the modulation of actomyosin contractibility and the reorganization of the actin cytoskeleton on the level of "target" cells were shown to favor their invasion into host cells[32, 34]. This process is distinct from cellular cannibalism that can also trigger NCADs through the activation of specific signaling pathways (such as phagocytosis-related signaling pathways that involve cytoskeleton remodeling cell division cycle 42 (CDC42), chemokine (C—X—C motif) ligand 1 (CXCL1) or chemokine (C—X—C motif) ligand 6 (CXCL6)) on host cells and leads to an active engulfment of target cells[33]. Once internalized, engulfed cells may be targeted by "host" lysosomal enzymes (such as cathepsins and granzymes) and eliminated through distinct lethal mechanisms that may involve several modulators of typical cell deaths (such as cytochrome c, caspases or autophagy-related (ATG) proteins). Entosis, a non-cell autonomous death, initially described after homotypic interactions between breast cancer cells, is cell-in-cell invasion mechanism that does not require the activation of caspases to eliminate engulfed cells[16]. Inversely the engulfment of natural killer (NK) by tumor cells initiates emperitosis, a programmed cell-in-cell death that requires caspase 3 activation and DNA fragmentation[30], revealing that engulfed cells can be eliminated through caspase-dependent or caspase independent processes.

Despite the intensive biological and pharmaceutical research implemented to better characterize cellular and biochemical processes associated with anticancer treatments, lethal mechanisms responsible for the therapeutic effects of radiotherapy, which is one of the most frequent anticancer treatment used in clinic, are still unknown. Lethal processes (such as apoptosis and mitotic catastrophe) that have been detected in response to ionizing radiation were not directly implicated in treatment efficiency[35], suggesting that additional cell death modalities that are still unknown may contribute to therapeutic effects of radiotherapy.

In this context, there is always a need to identify new treatments for reducing tumoral growth in patients suffering from cancer.

DESCRIPTION OF THE INVENTION

The present invention discloses the discovery of a new cell death mechanism (the cellular cannibalism) that has never been detected by others after RI or other anticancer treatments. Usually, in tumor vaccination experiments, cancer cells were exposed to cytotoxic anticancer treatment in vitro until 70% of the cells expose phosphatidylserine on the outer leaflet of the plasma membrane[48]. Interestingly, the present results reveal that chemical compounds selected on the basis of their ability to enhance IR-mediated cellular cannibalism (IRCCE) convert cancer cells into a vaccine that stimulate antitumor immune responses. More specifically, the present results reveal for the first time that the combination of IRCCE+IR elicit an IR-mediated anticancer immune response in absence of a significant increase of death of treated and irradiated cells (FIG. 5A), suggesting that cellular cannibalism or cellular cannibalism-associated signaling pathways contributes to the induction of tumor immunogenicity after irradiation.

Irradiation is commonly used for treating cancer. Often combined with chemotherapy and/or surgery, irradiation therapy encompasses both local and total body administration as well as a number of new advances, including radio-immunotherapy. The cytotoxic effect of irradiation on neoplastic cells arises from the ability of irradiation to cause a break in one or both strands of the DNA molecule inside the cells. Cells in all phases of the cell cycle are susceptible to this effect. However, the DNA damage is more likely to be lethal in cancerous cells because they are less capable of repairing DNA damage. Healthy cells, with functioning cell cycle checkpoint proteins and repair enzymes are far more likely to be able to repair the radiation damage and function normally after treatment. Nevertheless, irradiation brings side effects that are a burden for the patients. The side effects of irradiation are similar to those of chemotherapy and arise for the same reason, i.e., the damage of healthy tissues. Irradiation is usually more localized than chemotherapy, but this treatment is still accompanied by damages to previously healthy tissue. Many of the side effects are unpleasant, and irradiation also shares with chemotherapy the disadvantage of being mutagenic, carcinogenic and teratogenic in its own right. While normal cells usually begin to recover from treatment within two hours of treatment, mutations may be induced in the genes of the healthy cells. These risks are elevated in certain tissues, such as those in the reproductive system. Also, it has been found that different people tolerate irradiation differently. Doses that may not lead to new cancers in one individual may in fact spawn additional cancers in another individual. This could be due to pre-existing mutations in cell cycle checkpoint proteins or repair enzymes, but current practice would not be able to predict at what dose a particular individual is at risk. Common side effects of irradiation include bladder irritation, fatigue, diarrhea, low blood counts, mouth irritation, taste alteration, loss of appetite, alopecia, skin irritation, change in pulmonary function, enteritis, sleep disorders, and others.

It is highly advantageous to provide patients with a potentiating agent that triggers a synergistic effect with irradiation, thereby allowing the patient to be less exposed to irradiation therapy. This indeed reduces the above-mentioned side-effects, while achieving an improved beneficial result.

Altogether, it is disclosed that, given the highlighted importance of cellular cannibalism on the elimination of irradiated cancer cells and the increasing importance of the immune response in tumor response to irradiation, cellular cannibalism is a "desirable" death that should be favored during cancer treatments in order to efficiently eliminate irradiated cancer cells. This can be achieved by administering to the patients cellular cannibalism enhancers as demonstrated by the present inventors in the experimental part below.

Definitions

The term "irradiation therapy" is commonly used in the art to refer to multiple types of radiation therapy including internal and external radiation therapy, radio-immunotherapy, and the use of various types of radiation including X-rays, gamma rays, alpha particles, beta particles, photons, electrons, neutrons, radioisotopes, and other forms of ionizing radiation. As used herein, the terms "irradiation therapy", "radiation therapy", "radiotherapy", "radiation" and "irradiation" are inclusive of all of these types of radiation therapy, unless otherwise specified. There are different types of radiotherapy machines, which work in slightly different ways. The number and duration of the radiotherapy sessions depend on the type of cancer and where it is located in the body. A superficial skin cancer may need only a few short treatments, whereas a cancer deeper in the body may need more prolonged treatment.

The terms "suppressing tumor growth", "treating tumor growth", and "treating cancer", and the like refer to reducing the rate of growth of a tumor, halting tumor growth completely, causing a regression in the size of an existing tumor, eradicating an existing tumor and/or preventing the occurrence of additional tumors upon treatment with the compositions, kits or methods of the present disclosure. "Suppressing" tumor cell growth means any or all of the following states: slowing, delaying, and stopping tumor growth, as well as tumor shrinkage. "Delaying development" of a tumor means to defer, hinder, slow, retard, stabilize, and/or postpone development of the disease. This delay can be of varying lengths of time, depending on the history of the disease and/or individual being treated. Tumor cell growth can be assessed by any means known in the art, including, but not limited to, measuring tumor size, determining whether tumor cells are proliferating using a $^3$H-thymidine incorporation assay, or counting tumor cells.

As used herein, "synergy" or "synergistic effect" when referring to combination administration of a compound of the present disclosure in conjunction with radiation means that the effect of the combination is more than additive when compared to administration of the compound(s) and radiation alone.

"Potentiate" means, in the context of this application to enhance or increase the effect of, for example, a radiotherapy treatment, or to promote or strengthen, for example, a biochemical or physiological action or effect.

"Effective amount" refers to an amount of a compound as described herein that may be therapeutically effective to treat a cancer associated with the instant disclosure. The precise amount of these compounds required will vary with the particular compounds or derivatives employed, the age and condition of the subject to be treated, and the nature and severity of the condition. However, the effective amount may be determined by one of ordinary skill in the art with only routine experimentation. An effective amount of radiation can be determined without undue experimentation by one of ordinary skill in the art. Radiation parameters, such as dosing amount and frequency are well-known in the art.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"Pharmaceutically acceptable salts" refer to derivatives of the disclosed compounds wherein the parent compound is modified by making acid or base salts thereof. The compounds of this disclosure form acid and base addition salts with a wide variety of organic and inorganic acids and bases and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methyl benzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzene-sulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarale, and the like. Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

Alternative embodiments provide a method of potentiating radiotherapy cancer treatment as described, comprising the administration of a "slow-release formulation" that is able to release the active ingredient to the surroundings in a controlled, non-instant manner, time-dependent manner. This slow-release formulation may comprise a biodegradable polymer, for example selected from the group consisting of a homopolymer of lactic acid; a homopolymer of glycolic acid; a copolymer of poly-D,L,-lactic acid and glycolic acid; a water-insoluble peptide salt of a luteinizing hormone-releasing hormone (LHRH) analogue; a poly (phosphoester); a bis(p-carboxyphenoxy)propane (CPP) with sebacic acid copolymer; a polyanhydrides polymer; poly(lactide)-co-glycolide)polyethylene glycol copolymers; and an ethylene-vinyl acetate copolymer.

In some specific embodiments of the method, the slow-release formulation releases the IRCCE drug over a period of four or more weeks, alternatively over a period of one week or more, or alternatively over a period of few hours or more.

The methods, compositions formulations and uses described herein are suitable for both humans and animals, preferably mammals.

Thus, as used herein, the term "subject" relates to any mammal including a mouse, rat, pig, monkey and horse. In a specific embodiment, it refers to a human. A "subject in need thereof" or a "patient" in the context of the present invention is intended to include any subject that will benefit or that is likely to benefit from the methods and pharmaceutical compositions of the present invention. The subject may suffer from a cancer of any stage such that it could be an early non-invasive cancer or could be a late stage cancer that has already progressed to form metastases in the body.

"Patient" herein refers to animals, including mammals, preferably humans.

As used herein the term "cancer" is intended to include any form of cancer or tumors. Non-limiting examples of cancers include brain cancer (e.g., glioma), gastric cancer, head-and-neck cancer, pancreatic cancer, non-small cell lung cancer, small cell lung cancer, prostate cancer, colon cancer, non-Hodgkin's lymphoma, sarcoma, testicular cancer, acute non-lymphocytic leukemia and breast cancer. In a particular embodiment, the brain cancer is an astrocytoma, and more particularly, is glioblastoma multiforme; the lung cancer is either a small cell lung carcinoma or a non small cell lung carcinoma; and the head-and-neck cancer is squamous cell carcinoma or adenocarcinoma.

The present invention discloses that known and unknown drugs are able to enhance IR-mediated cellular cannibalism in vitro and in vivo in tumor-bearing animals.

As used herein, the terms "cellular cannibalism inducing drugs", "cellular cannibalism inducing agents", "cellular cannibalism inducing compounds" and "cellular cannibalism enhancers" designate compounds that are able to enhance the capacity of irradiation to trigger cellular cannibalism. Under these terms are designate compounds that are able to enhance IR-mediated cellular cannibalism (hereafter called IRCCE). The chemical structures of the selected cellular cannibalism modulators are presented in Table 1 and Table 2.

TABLE 1

| Molecules | Structures | Molecular weight (g/mol) |
|---|---|---|
| Myricetin | 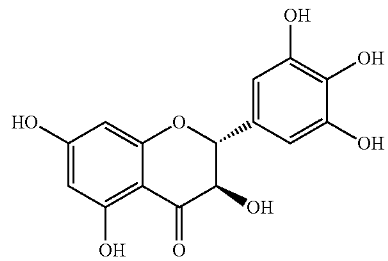 [SMILES: O=C1c2c(O)cc(O)cc2O[C@H](c2cc(O)c(O)c(O)c2)[C@H]1O] | 318.24 |
| Minaprine dihydrochloride | 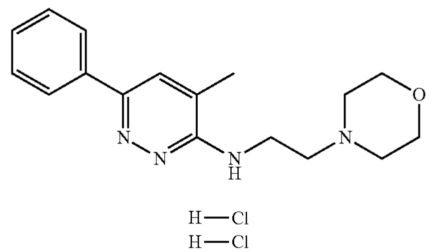 | 371.3 |
| Lanatoside C | 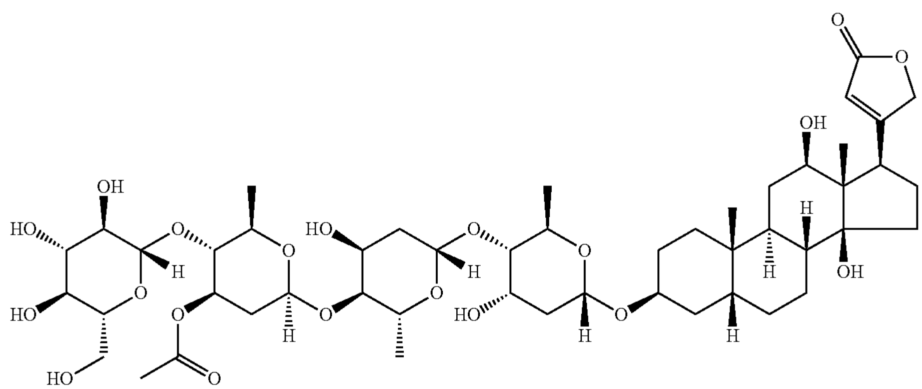 | 985.12 |
| Flurbiprofen | 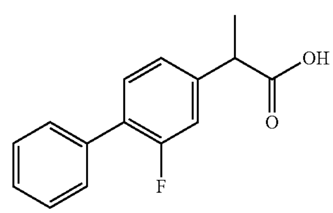 [SMILES: CC(C(=O)O)c1ccc(-c2ccccc2)c(F)c1] | 244.26 |
| Mebhydroline 1,5-naphtalene-disulfonate | 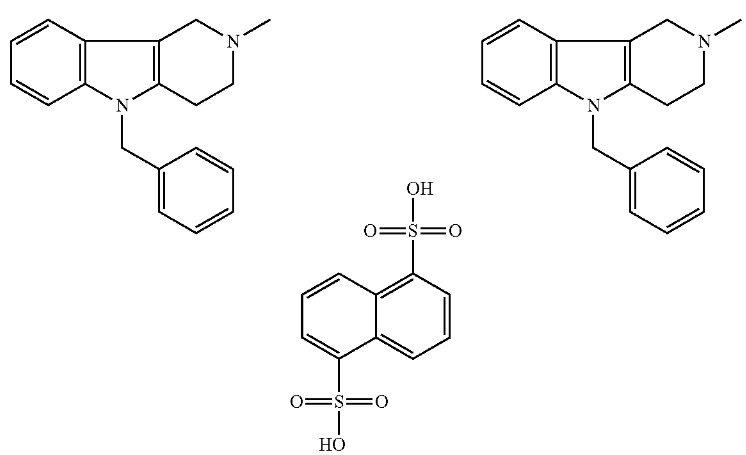 [SMILES: CN1CCc2c(c3ccccc3n2Cc2ccccc2)C1 ; O=S(=O)(O)c1cccc2c(S(=O)(=O)O)cccc12 ; CN1CCc2c(c3ccccc3n2Cc2ccccc2)C1] | 420.52 |

TABLE 1-continued
| Molecules | Structures | Molecular weight (g/mol) |
|---|---|---|
| Azaguanine-8 | 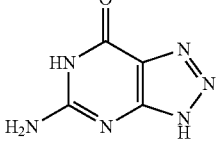 | 152.11 |
| Digitoxigenin | 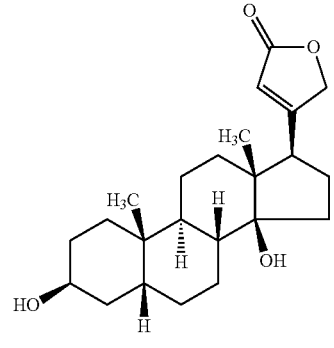 | 390.51 |
| Doxorubicin hydrochloride | 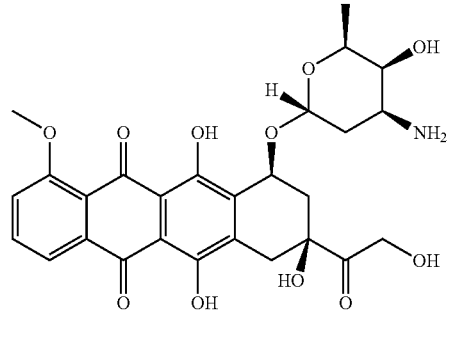 | 579.98 |
| Digoxin | 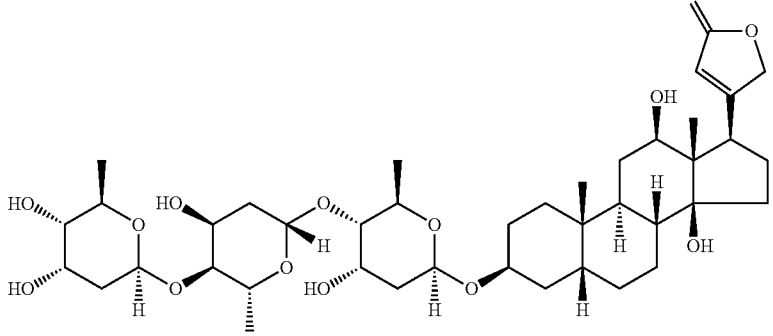 | 780.949 |

TABLE 2

| Molecules | Structures | Molecular weight (g/mol) |
|---|---|---|
| RN-1-001 | 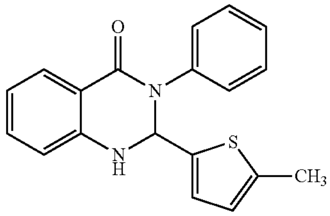 [SMILES: Cc1ccc(C2Nc3ccccc3C(=O)N2c2ccccc2)s1] | 320 |
| VP43 | 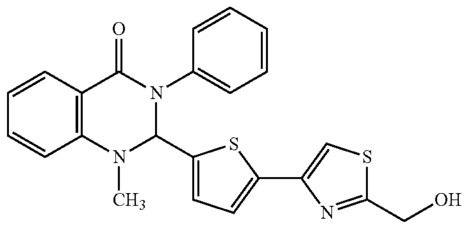 [SMILES: CN1c2ccccc2C(=O)N(c2ccccc2)C1c1ccc(-c2csc(CO)n2)s1] | 425 |
| VP450 | 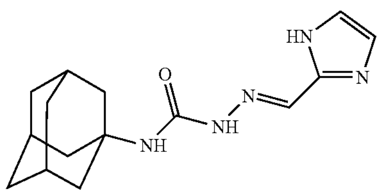 [SMILES: O=C(N/N=C/c1ncc[nH]1)NC12CC3CC(CC(C3)C1)C2] | 287 |
| SG6163F | 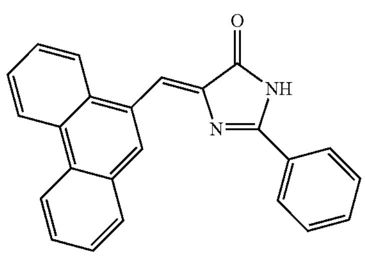 [SMILES: O=C1NC(c2ccccc2)=N/C1=C\c1cc2ccccc2c2ccccc12] | 348 |
| RN-1-026 | 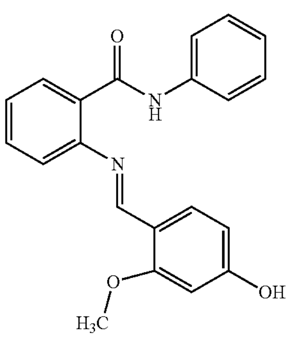 [SMILES: COc1cc(O)ccc1/C=N/c1ccccc1C(=O)Nc1ccccc1] | 346 |
| VP331 | 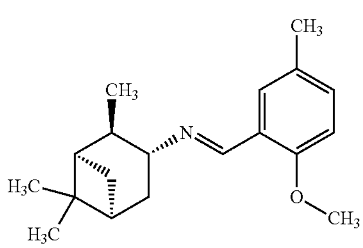 | 350 |

TABLE 2-continued

| Molecules | Structures | Molecular weight (g/mol) |
|---|---|---|
| LOPA87 | (structure shown) | 291 |

In total, the present inventors discovered 16 efficient cellular cannibalism enhancer compounds, namely: 8-Azaguanine, Mebhydroline 1,5-napthalene disulfonate salt, Flurbiprofen, Minaprine dihydrochloride, Myricetin, Digoxin, Digitoxin, Lanatoside, Doxorubicine hydrochloride, LOPA87, VP331, RN-1-026, SG6163F, VP450, VP43. A number of interesting compounds have been also identified. They are for examples analogs of LOPA87 (LOPA90, LOPA93, LOPA 94, LOPA 101, LOPA104, LOPA105, LOPA106) and analogs of SG6143F (SG6144, SG6146 and SG6149).

Minaprine dihydrochloride ($C_{17}H_{22}N_4O$, amino-phenylpyridazine antidepressant). Minaprine dihydrochloride is a psychotropic drug which has proved to be effective in the treatment of various depressive states. Like most antidepressants minaprine antagonizes behavioral despair. Minaprine is an amino-phenylpyridazine antidepressant reported to be relatively free of cardiotoxicity, drowsiness, and weight gain. More specifically, minaprine is an amino-phenylpyridazine antidepressant reported to be relatively free of cardiotoxicity, drowsiness, and weight gain. Similar to other antidepressant treatments, minaprine attenuates the beta-adrenergic receptor function. Studies have also shown that minaprine improves memory consolidation and that repeated drug administration leads to potentiation of this effect. Moreover, the effects of minaprine on memory consolidation are related to its dopaminergic action. Minaprine binds to serotonin type 2 receptors and to dopamine D1 and D2 type receptors. It also binds to the serotonin reuptake pump. Therefore, minaprine blocks the reuptake of both dopamine and serotonin. It is also, to a slight degree, cholinomimetic. Thus it may exhibit both mood-brightening and nootropic properties. It also acts as a reversible inhibitor of MAO-A (RIMA). It has also been found to inhibit acetylcholinesterase. The preparation of this compound is illustrated in U.S. Pat. No. 4,169,158, which is incorporated herein by reference.

Chemical Compounds Obtained from the Screened Library

LOPA87, VP331, RN-1026, SG6163F, VP450 and VP43 have been obtained from the CEA library. 7 analogs of LOPA87 (LOPA90, LOPA93, LOPA 94, LOPA 101, LOPA104, LOPA105, LOPA106) and 3 analogs of SG6163F (SG6144, SG6146 and SG6149) were also identified.

Analogs of Minaprine Dihydrochloride:

Analogs of Minaprine dihydrochloride that can be used in the composition of the invention are 3-aminoalkylamino-4-alkyl-6-aryl-pyridazines of the formula:

(structure of formula I shown)

wherein:

R1 is a hydrogen atom or a lower alkyl group;

R2 is an aryl or substituted aryl group;

N is 2 or 3; and

Y and Z may be the same or different lower alkyl groups, or

is a heterocyclic radical wherein Z and Y are lower alkylene groups cyclized to form a ring which contains an oxygen atom linked between the alkylene groups and the nitrogen atom attached to the opposite end of each alkylene group.

In formula (I), the lower alkyl groups may suitably contain from 1 to 3 carbon atoms, and the lower alkylene groups, 2 carbons each; and when R1 is a lower alkyl group, it is preferably a methyl group. Group R2 may be a phenyl, substituted phenyl or naphthyl group. When

is a heterocyclic radical, it may suitably be a morpholino, piperidino or pyrrolidino group.

The analogs also include the acid addition salts of the compounds of formula (I) formed by reaction of the base with a suitable organic or inorganic acid such as tartaric acid or hydrochloric acid to name two well-known representative acids of this group.

Other inhibitors of monoamine oxidase A can be used as analogs of Minaprine hydrochloride. They are for example moclobemide or toloxatone. Non-selective IMAO can also be used: isocarboxazid, nialamide, phenelzine, tranylcypromine, iproniazide, or iproclozide.

Aspects of the Invention

The present invention discloses the in vitro use of the above-identified compounds (highlighted in Tables 1 & 2) for enhancing IR-mediated cellular cannibalism (IRCCE) of cancer cells.

This part of the invention is performed in vitro. As disclosed herein, the terms "in vitro" and "ex vivo" are equivalent and refer to studies or experiments that are conducted using biological components (e.g. cells or population of cells) that have been isolated from their usual host organisms (e.g. animals or humans). Such isolated cells can be further purified, cultured or directly analyzed to assess the presence of the mutant proteins. These experiments can be for example reduced to practice in laboratory materials such as tubes, flasks, wells, eppendorfs, etc. In contrast, the term "in vivo" refers to studies that are conducted on whole living organisms.

IR-mediated cellular cannibalism can be assessed by any conventional means. In particular, this activity can be assessed by studying the cells under the microscope (by immunofluorescence or immunohistochemistry) and by visually detecting cell engulfment events or cell-in-cell systems. Alternatively, it can be assessed by measuring, in said cell, the expression level of a protein selected from the group consisting of: p53, p53β, p53γ, and N-terminal isoforms of p53 that lack the N-terminal transactivating domain, such as Δ40TP53 and Δ133TP53, or by measuring the expression level or the activity of the purinergic P2Y2 receptor, and/or by measuring the extracellular ATP secreted by said cells, as disclosed in WO2014/006227 which is incorporated herein by reference.

The compounds of the invention can also be used in vivo.

In this case, the compounds of the invention can be administered to the patients in a pharmaceutical composition further containing pharmaceutically acceptable adjuvants. The "pharmaceutical composition of the invention" therefore contains an efficient amount of at least one of the compound of the invention (see Table 1 & 2 above, such as Minaprine dihydrochloride), or analogs thereof, and pharmaceutically acceptable adjuvants or carriers. Examples of non-aqueous adjuvants are propylene glycol, polyethylene glycol, vegetable oil and injectable organic esters such as ethyloleate. Other pharmaceutically acceptable adjuvants include aqueous solutions and non-toxic excipients including salts, preservatives, buffers and the like. Intravenous vehicles include fluid and nutrient replenishers. The compositions may also include preservatives such as antimicrobial agents, anti-oxidants, chelating agents and inert gases. The pH and exact concentration of the various components of the pharmaceutical composition can be adjusted according to well-known parameters.

The in vivo administration of the compounds of the invention (among which Minaprine dihydrochloride) or of the composition of the invention (containing Minaprine dihydrochloride) is intended to reduce the tumor growth in subjects suffering from cancer.

It can also enhance the tumor immunogenicity in subjects that will or that have undergone a radiotherapy treatment. While not being bound to any particular theory, it is believed that these compounds work synergistically with radiation therapy by favoring cellular cannibalism and thereby the exposure of particular epitopes that induce a significant protective anticancer immune response.

The present disclosure targets the use of the compounds disclosed in Tables 1 & 2 above (among which Minaprine dihydrochloride), or of their analogs, for manufacturing a pharmaceutical composition intended to be administered to a subject in need thereof.

It is also drawn to the use of the compounds disclosed in Tables 1 & 2 above (among which Minaprine dihydrochloride), or of their analogs, for manufacturing a pharmaceutical composition intended to treat a subject in need thereof.

The present invention also discloses the compounds in Tables 1 & 2 above (among which Minaprine dihydrochloride) or their analogs, or any pharmaceutical composition containing same,
- for their use for enhancing IR-mediated cellular cannibalism in patients suffering from cancer,
- for their use for enhancing tumor immunogenicity in subjects that will or that have received a radiotherapy treatment,
- for their use for inducing a significant protective anticancer immune response in subjects that will or that have received a radiotherapy treatment,
- for their use for potentiating a radiotherapy treatment in a subject in need thereof,
- for their use for treating cancer, in conjunction with radiotherapy, in a subject in need thereof.

Importantly, administering the compositions of the invention enables to reduce the dose of irradiation and therefore results in the alleviation of the side effects incurred by the radiation treatment.

The pharmaceutical compositions of the present invention containing Minaprine dihydrochloride can be administered in the form of injectable compositions (e.g., intravenously, intramuscularly, subcutaneously and intra-articularly), either as liquid solutions or suspensions; solid forms suitable for solution in, or suspension in, liquid prior to injection also may be prepared. These preparations also may be emulsified.

Said pharmaceutical compositions can also be administered by other routes such as orally, nasally, rectally, topically, intratumorally, intravenously, intramuscularly, subcutaneously, sublingually, intrathecally, intraperitoneally, intra-articularly or intradermally. Preferably, the route of administration is intravenously, intra-arterially or orally. Preferably, the pharmaceutical compositions are administered intravenously or intra-arterially. More preferably, they are administered intratumorally.

In specific embodiments, when the composition of the present invention is for oral administration, the composition of the invention is in a tablet, a solution or capsule such as a soft gel capsule for example. In other specific embodiments, when the composition of the present invention is for oral administration, it has an enteric coating. In other specific embodiments, when the composition of the present invention is for oral administration, it is an oil-based syrup.

In a particular embodiment, the compounds of the invention are administered in a slow-release formulation.

The compositions of the present invention are administered in amounts and at frequencies sufficient to treat cancer. A subject's progress can be determined by measuring and observing changes in the concentration of cancer markers; by measuring the actual size of the tumor over time and/or by determining any other relevant clinical markers which are well-known in the art. The determination, measurement, and evaluation of such characteristics and markers associated with clinical progress are well-known to those of ordinary skill in the art.

Figure 6:
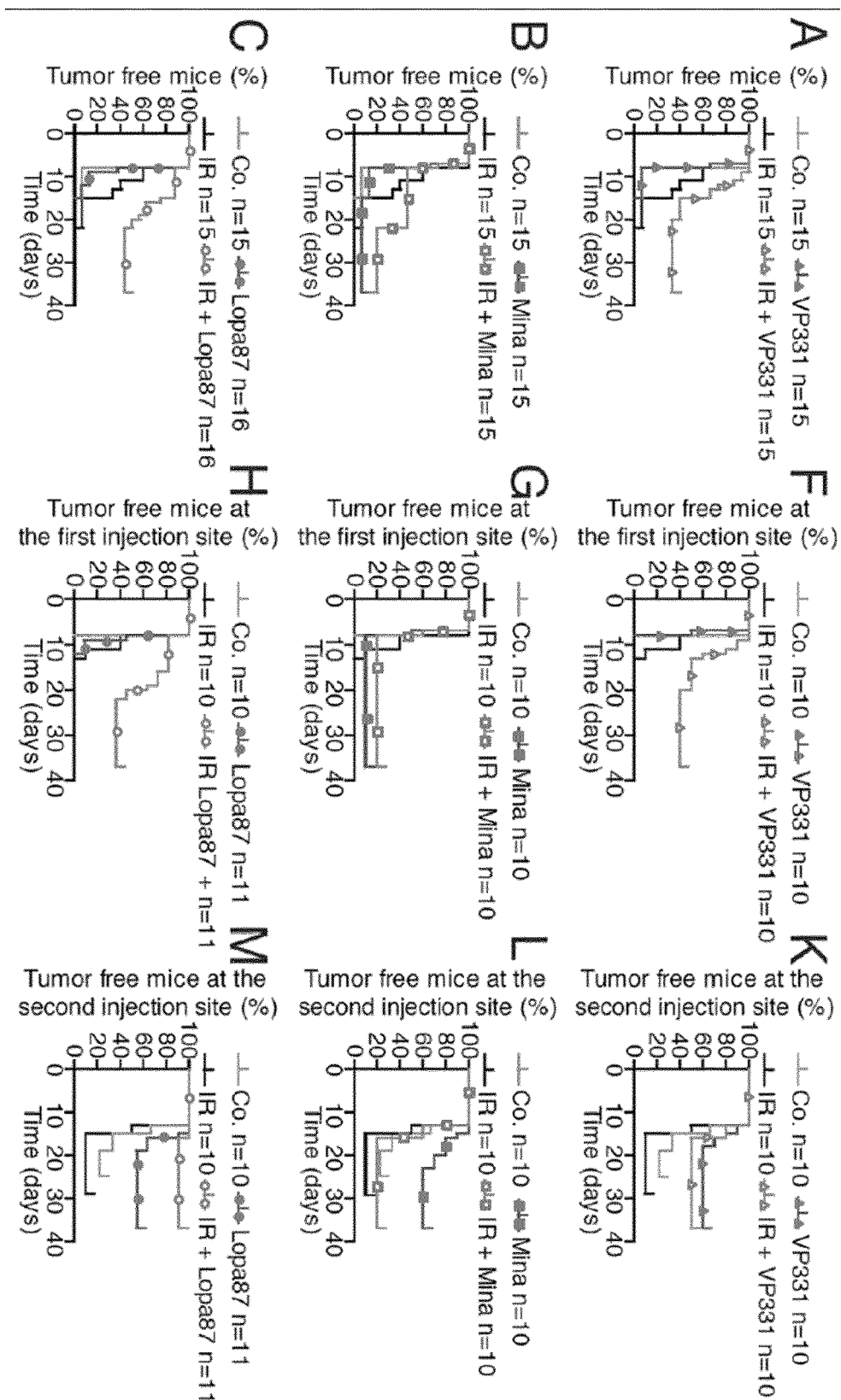
Figure 6:
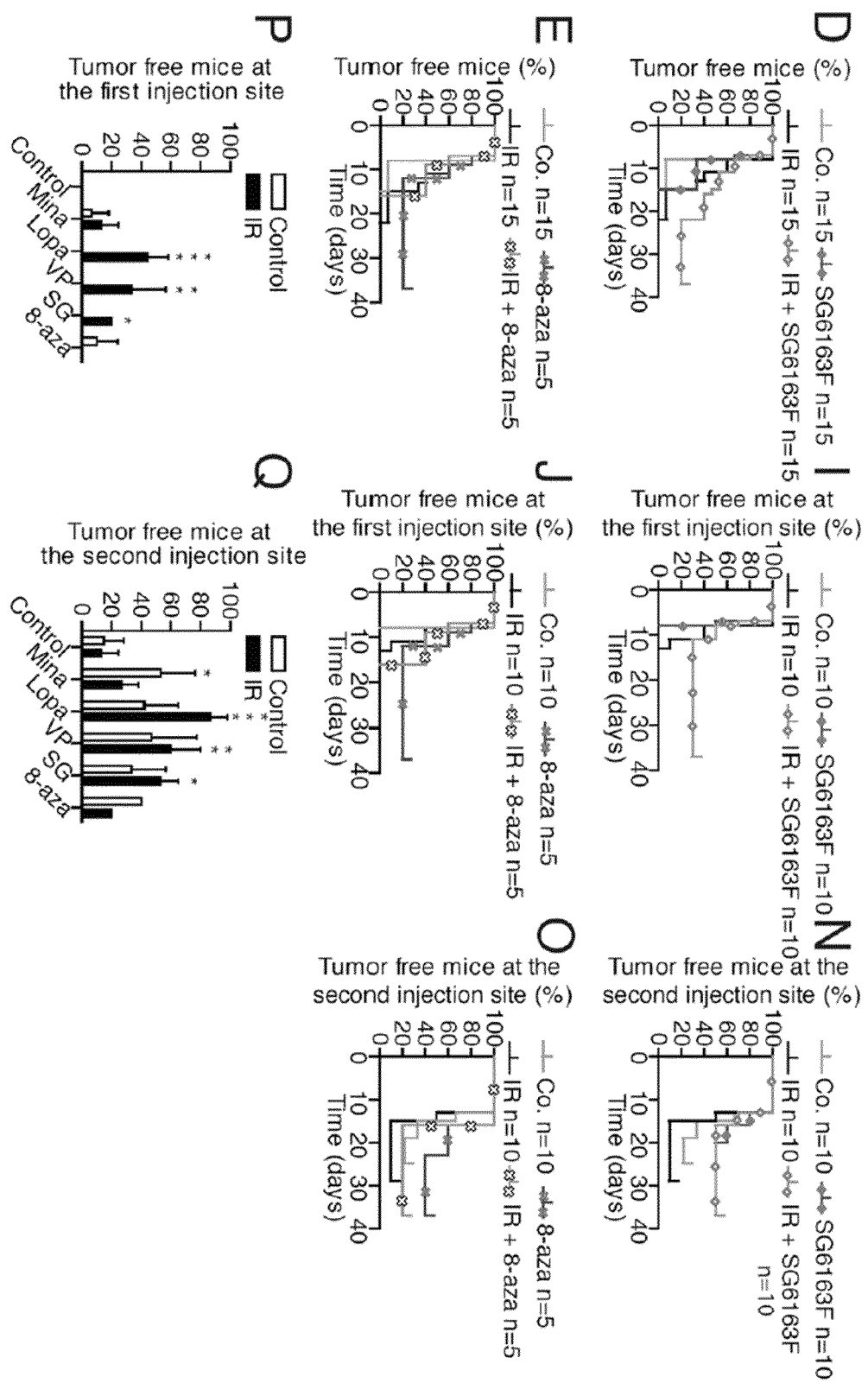
Figure 7:
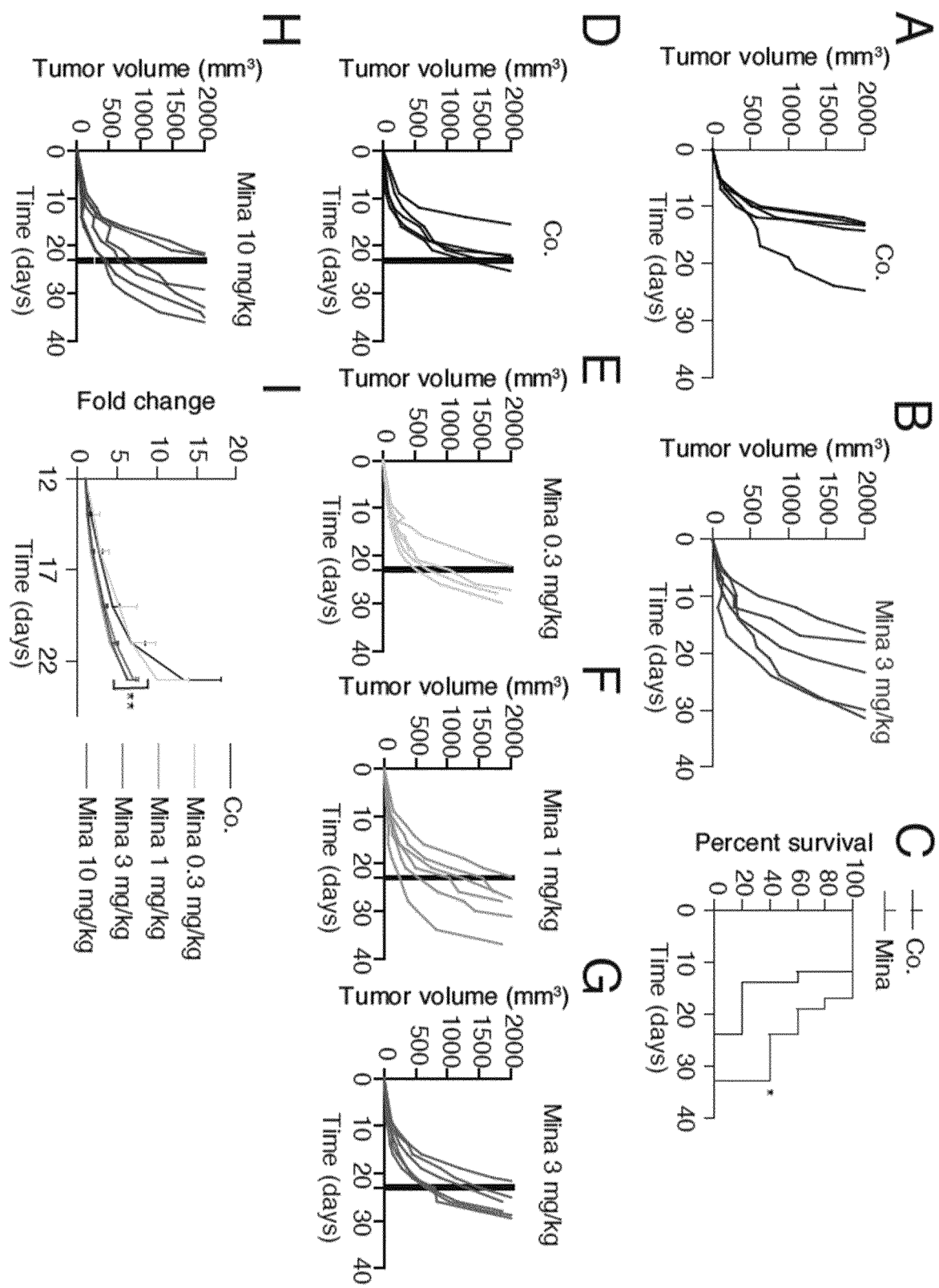

As shown in FIGS. 6 and 7, the present inventors observed that the administration of minaprine dihydrochloride alone has intrinsic protective effects against tumor development. Consequently, minaprine dihydrochloride does not need to be combined with a radiotherapy treatment, it is efficient on its own. This is a very surprising result, since minaprine dihydrochloride is known as an anti-depressant drug, and no anti-tumoral effect has ever been reported for this drug.

In a third aspect, the present invention therefore addresses minaprine dihydrochloride, or any pharmaceutical composition containing same,
- for its use for treating patients suffering from cancer,
- for its use for inducing a significant protective anticancer immune response in cancer patients.

It also relates to the use of minaprine dihydrochloride for preparing a medicament that is intended to prevent or treat cancer in a subject in need thereof.

In this third aspect, minaprine dihydrochloride is preferably not used in combination with radiotherapy treatment (whether a third type of anticancer treatment is or not present). Minaprine dihydrochloride may be used in combination with one or more anticancer treatment(s) other than radiotherapy (for instance chemotherapy and/or immunotherapy), provided that radiotherapy is not used. In a embodiment, minaprine dihydrochloride is however not used in combination with any other anticancer treatment, and is thus the only compound with anticancer efficiency administered to the patient suffering from cancer.

Effective doses of minaprine dihydrochloride that can be safely administered to humans when administered by oral are comprised between: 50 mg and 500 mg per day, preferably between 100 mg and 400 mg per day, more preferably around 200 mg per day.

Effective doses of minaprine dihydrochloride that can be safely administered to humans when administered intratumorally are comprised between: 0.3 mg/kg and 30 mg/kg.

All the embodiments disclosed above for the pharmaceutical compositions are transposable to this particular use.

Methods of Treatment

The present invention also targets a method for treating cancer patients, comprising administering to said patients an effective amount of minaprine dihydrochloride, or any pharmaceutical composition containing same. As a matter of fact, said anti-depressant drug has been shown by the inventors to have a significant protective anticancer immune response on its own.

Preferably, the above method does not use minaprine dihydrochloride in combination with radiotherapy treatment (whether a third type of anticancer treatment is or not present), and thus does not comprise a radiotherapy step. The method may combine minaprine dihydrochloride with one or more anticancer treatment(s) other than radiotherapy (for instance chemotherapy and/or immunotherapy), provided that radiotherapy is not used. In some embodiments of the above method, minaprine dihydrochloride is however not used in combination with any other anticancer treatment, and the method thus does not comprise any step of administering another anticancer treatment than minaprine dihydrochloride. In such a method, minaprine dihydrochloride is thus the only compound with anticancer efficiency administered to the patient suffering from cancer.

FIGURE LEGENDS

FIG. 1 Cell Death Profiling by quantitative imaging flow-cytometry. (A) Principle of cell death profiling by quantitative flow imaging. (B) Validation of multiparametric and simultaneous detection of cell death modalities by quantitative imaging flow-cytometry induced by gamma-irradiation. Before co-culture, treated HCT116 cells and non-treated HCT116 cells were respectively labeled with CMFDA (green/light grey) or CMTMR (red/dark grey) fluorescent vital probes. After 24 hours of co-culture, HCT116 cells were analysed for non-cell autonomous death (NCAD) (by detecting engulfment of CMTMR- or CMFDA-labeled HCT116 cells), for phosphatidylserine (PS) exposure (using Biotin-AnnexinV and BV786-Streptavidin), for loss of plasma integrity (by following with DRAQ7 uptake) and for DNA content (using Hoechst 33342). Using quantitative flow-cytmotery, the simultaneous detection of NCA deaths and of typical cell deaths (Type I, II and III) on both non-treated and treated HCT116 cells will determine the cell death profiling obtained after cancer treatment. Representative images are shown (scale, 20 µm).

Figure 2:
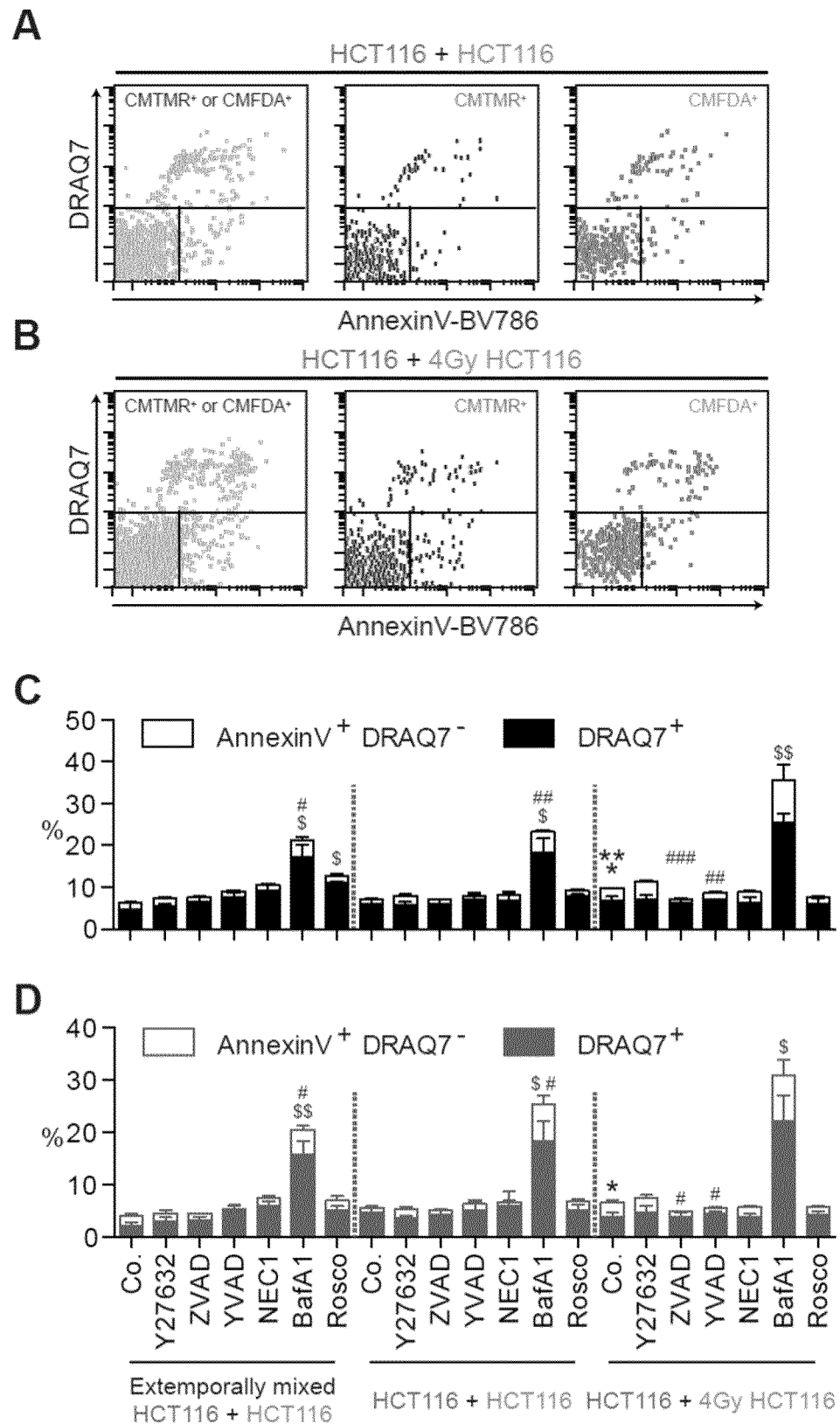
Figure 2:
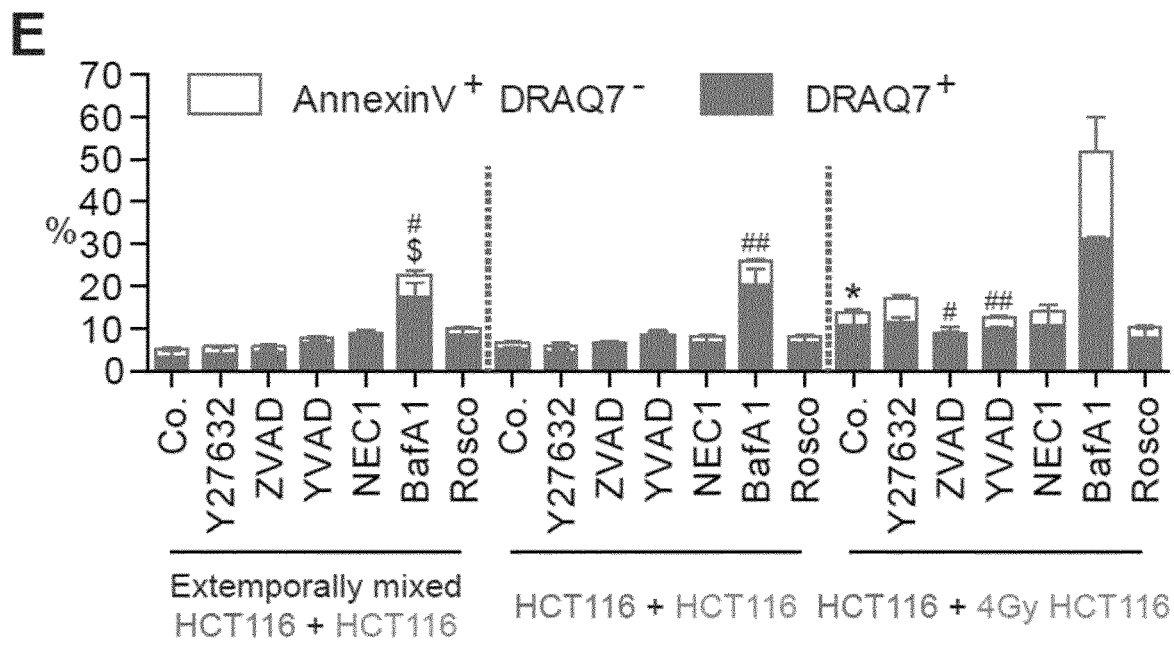
Figure 2:
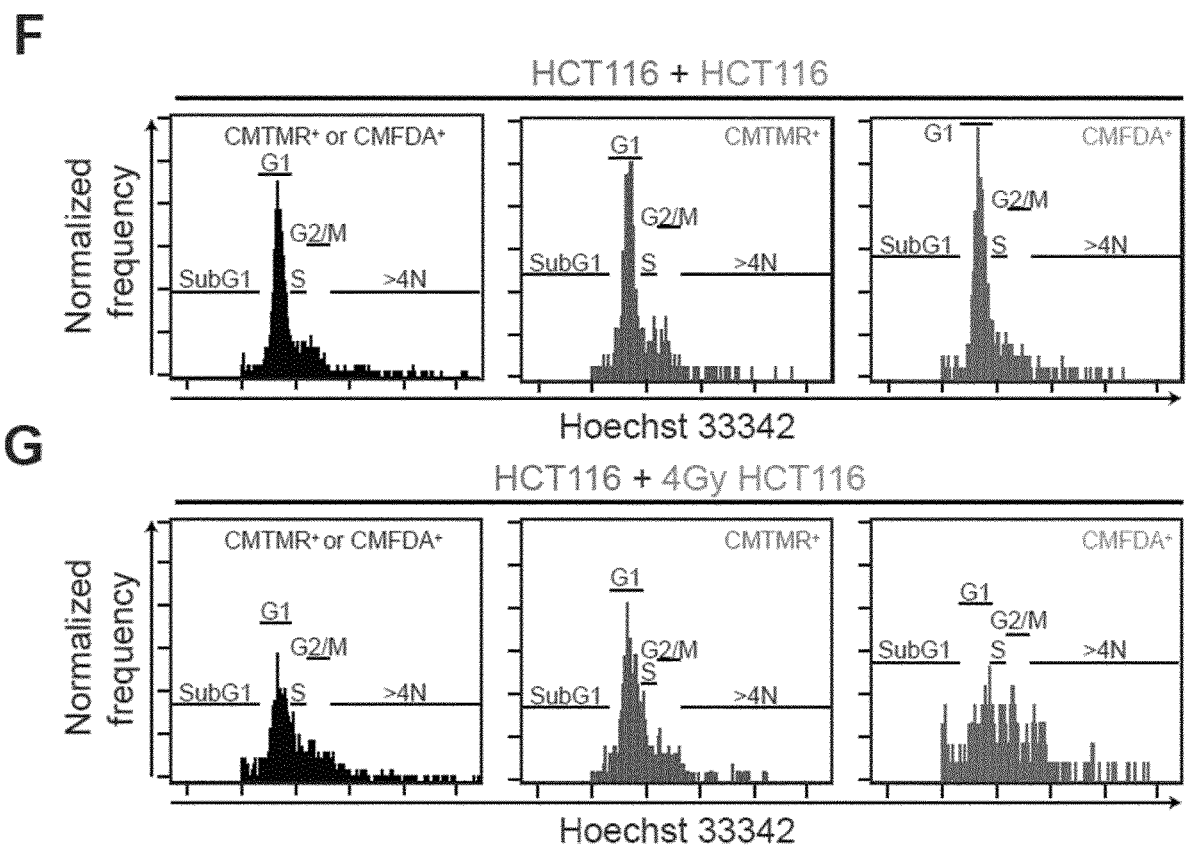
Figure 2:
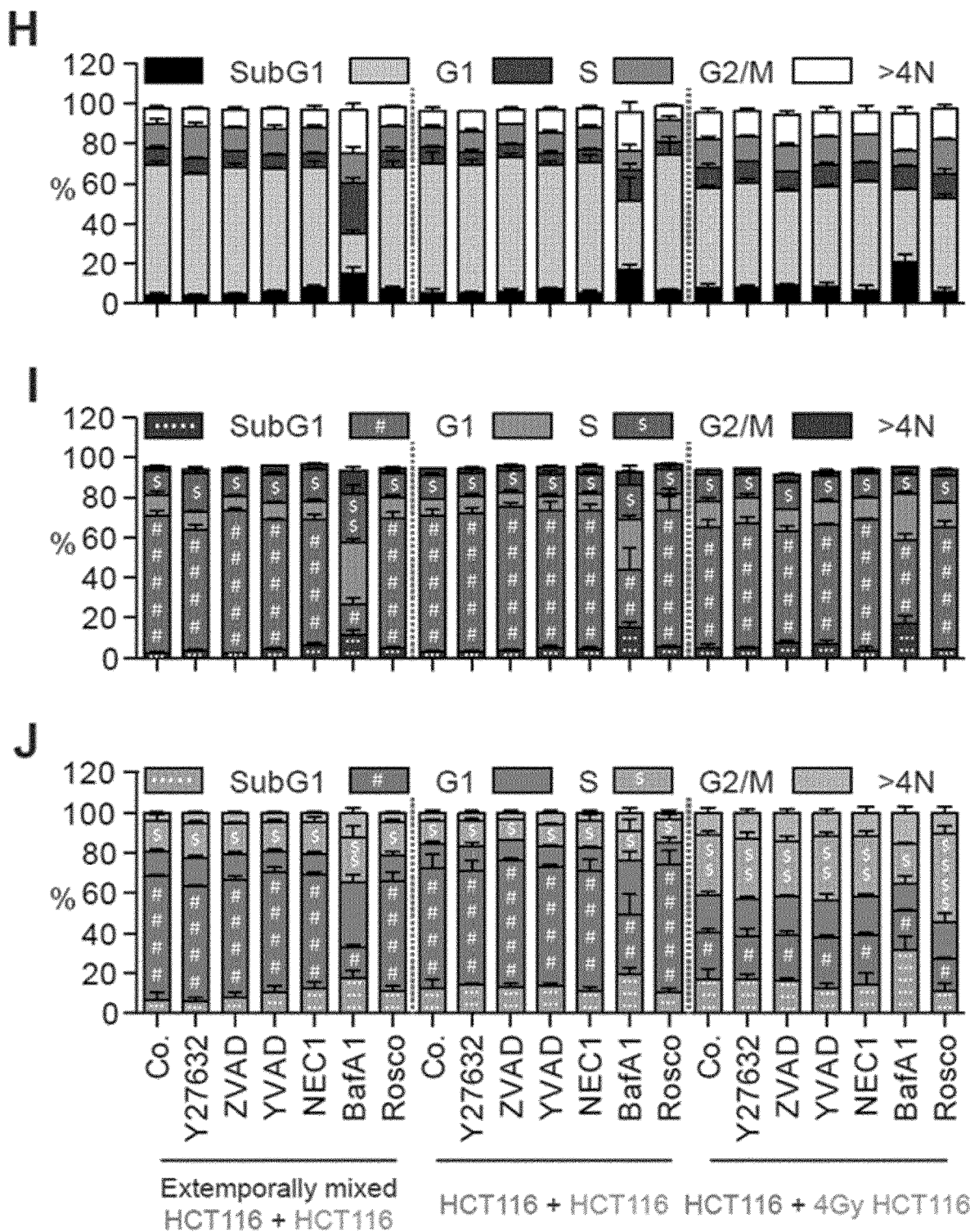

FIG. 2 Detection of γ-irradiation-elicited cell autonomous death modalities by quantitative imaging flow-cytometry. (A-E) Detection and quantification of plasma membrane integrity loss and PS exposure observed after 24 hour co-culture of untreated (red/dark grey) CMTMR-labeled HCT116 cells and untreated (green/light grey) CMFDA-labeled HCT116 cells (A, C-E), of untreated (red/dark grey) CMTMR-labeled HCT116 cells and untreated (green/light grey) CMFDA-labeled HCT116 cells that have been extemporally mixed (C-E) or after 24 hour co-culture of untreated (red/dark grey) CMFDA-labeled HCT116 cells with (green/light grey) CMFDA-labeled HCT116 cells (green) that have been irradiated with 4 grays of γ-ionizing radiation (B-E). The co-cultures have been performed in presence or absence of the indicated pharmacological death effector inhibitors. The detection of plasma membrane integrity (with DRAQ7) and PS exposure (with BV786-streptavidin/Annexin V biotin) have been analyzed for the untreated (red/dark grey) CMTMR$^+$ HCT116 cells, for untreated (green/light grey) CMFDA$^+$ HCT116 cells, for treated (green/light grey) CMFDA$^+$ HCT116 cells and for total cell population (CMTMR$^+$ or CMFDA$^+$ HCT116 cells). Representative dot plots (A,B) and quantitative data (C-E) are shown (means±SEM, n=3). (F,G) Representative cell cycle distributions of untreated (red/dark grey) CMTMR$^+$ HCT116 cells, untreated (green/light grey) CMFDA$^+$ HCT116 cells, treated (green/light grey) CMFDA$^+$ HCT116 cells and for total cell population (CMTMR$^+$ or CMFDA$^+$ HCT116 cells) obtained after 24 hour co-culture of untreated (red/dark grey) CMTMR-labeled HCT116 cells with untreated (green/light grey) CMFDA-labeled HCT116 cells (F, H-J), of untreated (red/dark grey) CMTMR-labeled HCT116 cells and untreated (green/light grey) CMFDA-labeled HCT116 cells that have been extemporally mixed (H-J) or after 24 hour co-culture of untreated (red/dark grey) CMTM-labeled HCT116 cells with (green/light grey) CMFDA-labeled HCT116 cells (green/light grey) that have been irradiated with 4 grays of γ-ionizing radiation (G-J) are shown. Quantitative data of cell cycle analysis are shown in (H-J) (means±SEM, n=3). * or # or $ represents p<0.05, ## or $$ p<0.01, *** or ###p<0.001.

Figure 3:
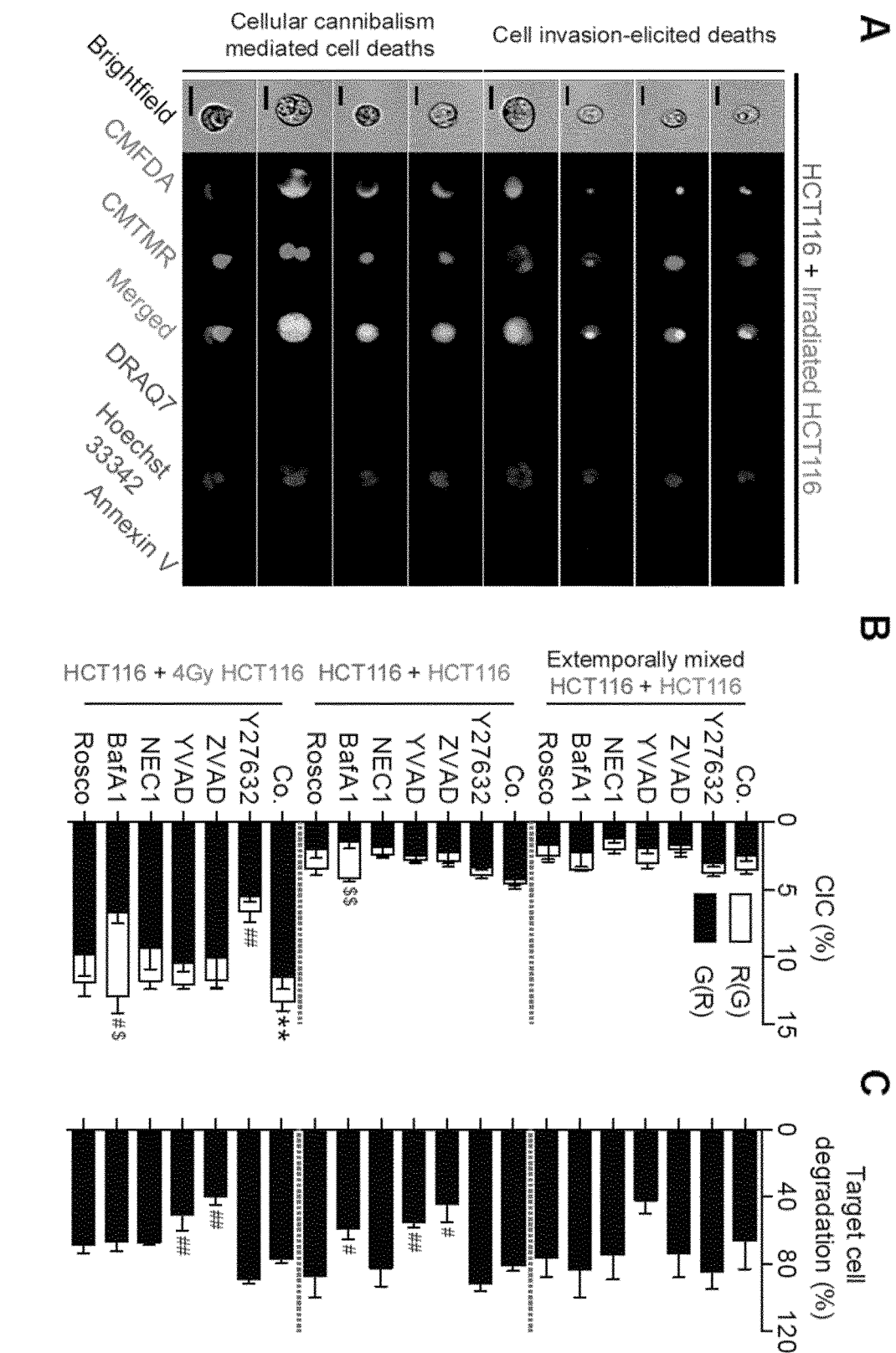
Figure 3:
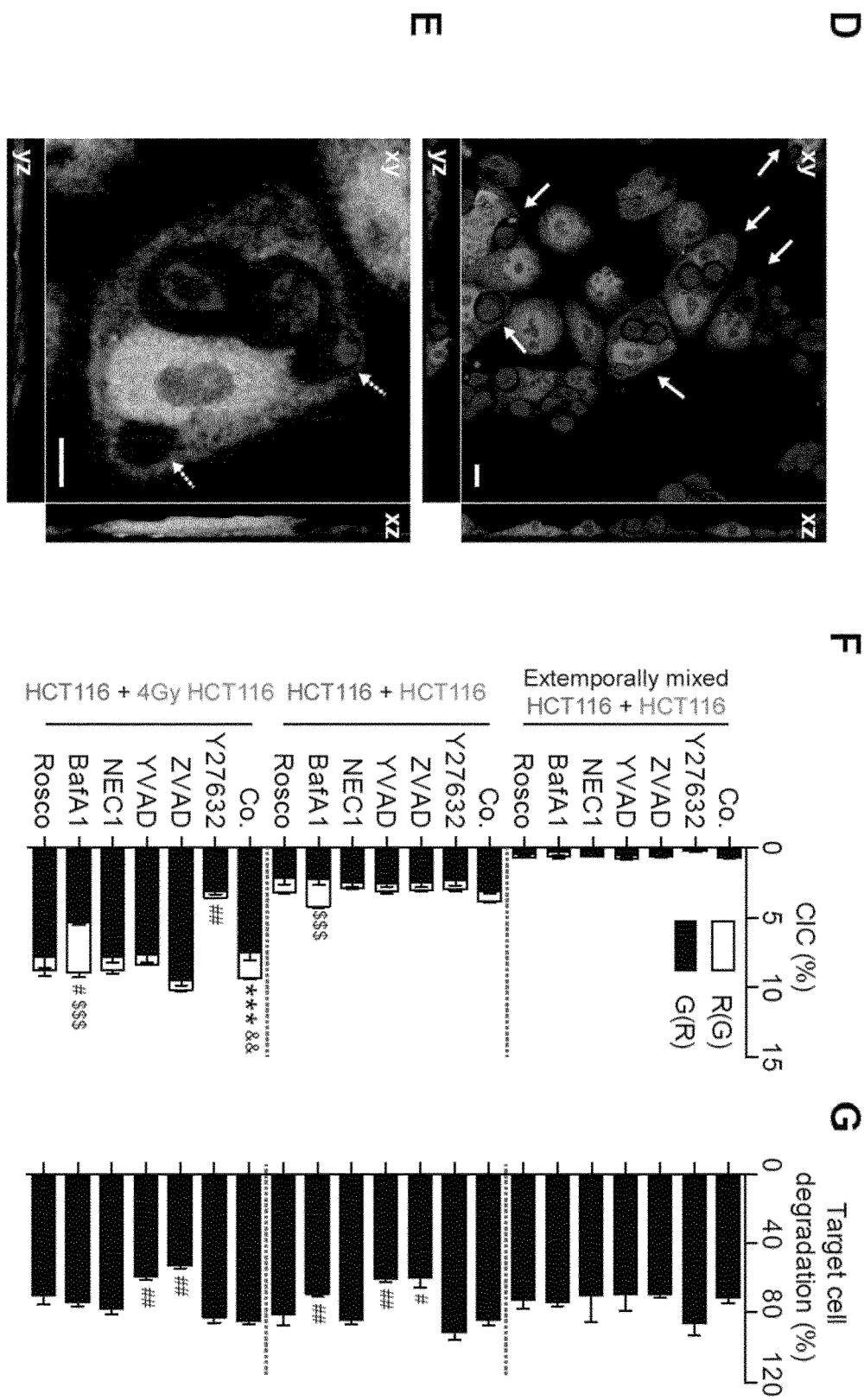

FIG. 3 Detection of γ-irradiation-elicited non-cell autonomous death modalities by quantitative imaging flow-cytometry and confocal fluorescence microscopy. (A-G) Cell-in-cell structures and target cell degradation were determined by quantitative imaging (A-C) and confocal fluorescent microscopy (D-G) after 24 hour co-culture of untreated (red/dark grey) CMTM-labeled HCT116 cells with (green/light grey) CMFDA-labeled HCT116 cells that have been irradiated with 4 grays of γ-ionizing radiation (A), coculture of untreated (red/dark grey) CMTMR-labeled HCT116 cells with untreated (green/light grey) CMFDA-labeled HCT116 cells (B, C) or on CMTMR labeled (red/dark grey) HCT116 cells and untreated (green/light grey) CMFDA-labeled HCT116 cells that have been extemporally mixed (B, C). As previously described, cells have been sequentially labeled after co-cultures with specific fluorescent probes like BV786-streptavidin-Annexin V biotin, DRAQ7, and Hoechst 33342. Then, (red/dark grey) CMTMR-labeled HCT116 cells internalizing (green/light grey) CMFDA-labeled HCT116 cells (noted R(G)), and (green/light grey) CMFDA-labeled HCT116 cells internalizing (red/dark grey) CMTMR-labeled HCT116 cells (noted G(R)) were detected. Representative images are shown in (A) (scale, 20 µm). Frequencies of Cell-in-Cell structures (B) and target cell degradation (C) are reported (means±SEM, n=3). Representative confocal images of cell-in-cell structures (white arrow) (D) and target cell degradation (white dotted arrow) (E) detected during co-culture of untreated (red) CMTMR-labeled HCT116 cells with untreated or γ-irradiated (green) CMFDA-labeled cells are shown (scale bar=10 µm). (F-G) Frequencies of cell-in-cell structures showing (red/dark grey) CMTMR-labeled cells internalizing (green/light grey) CMFDA-labeled cells (noted R(G)), and (green/light grey) CMFDA-labeled cells internalizing (red/dark grey) CMTMR-labeled cells (noted G(R)) (F) and target cell degradation (G) have been determined (means±SEM, n=3); # or $ represents p<0.05, ## or $$ p<0.01, *** or $$$ or ### p<0.001.

Figure 4:
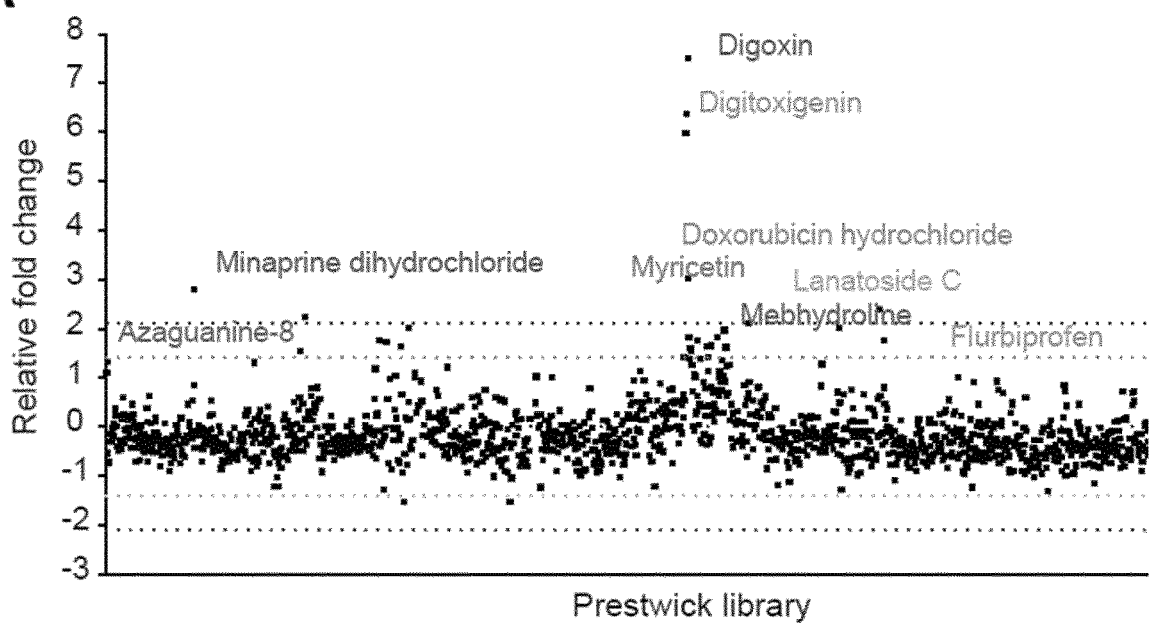
Figure 4:
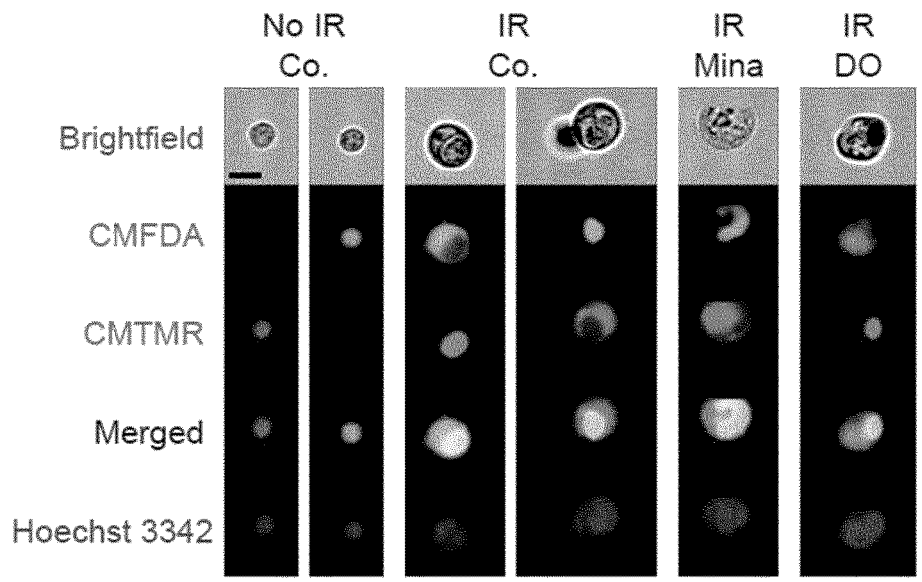
Figure 4:
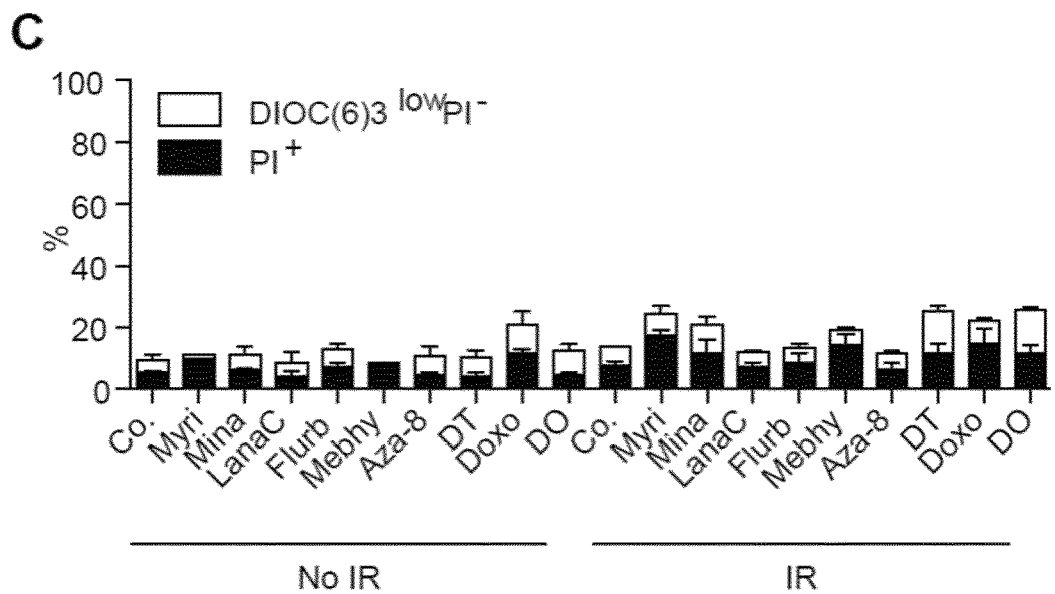
Figure 4:
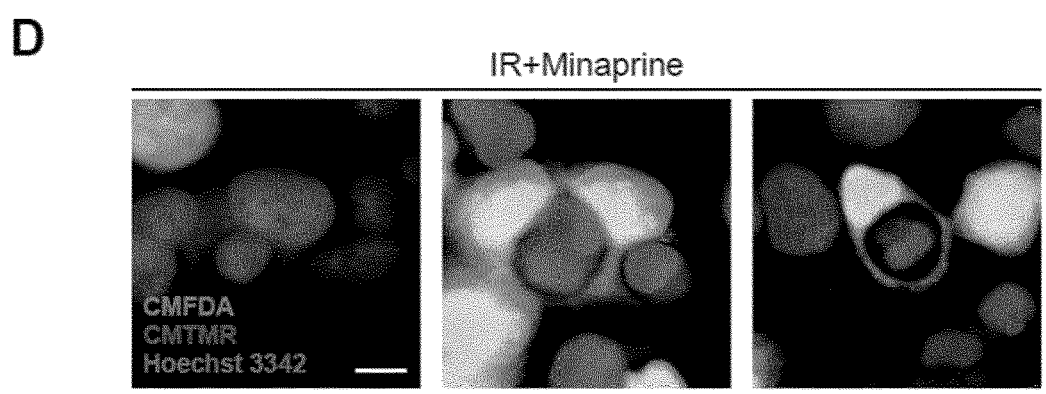
Figure 4:
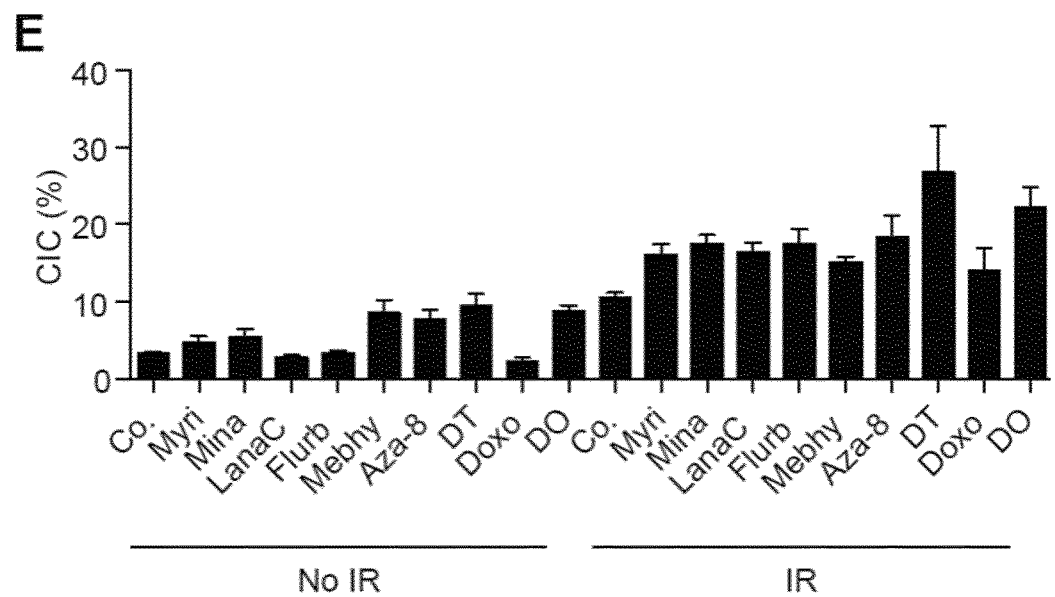
Figure 4:
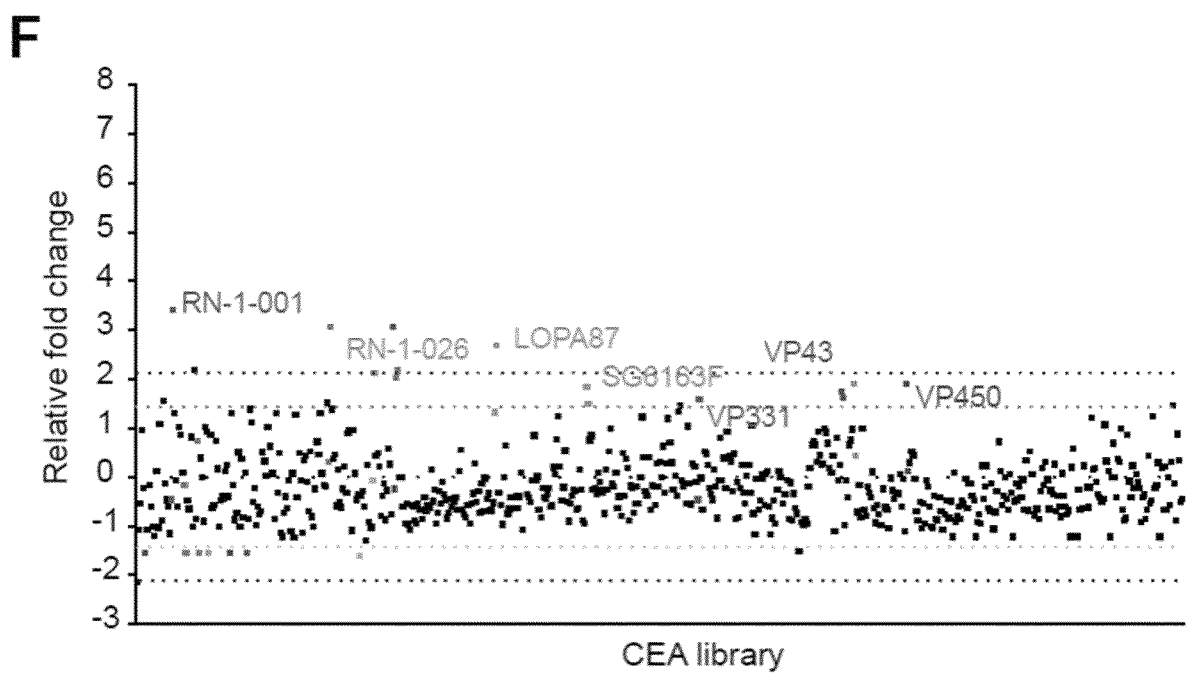
Figure 4:
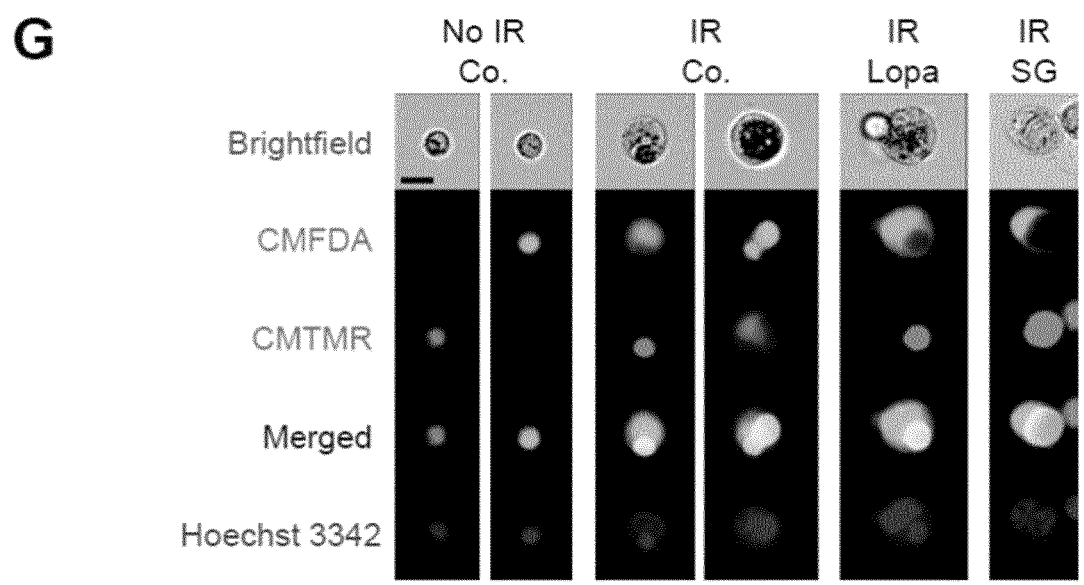
Figure 4:
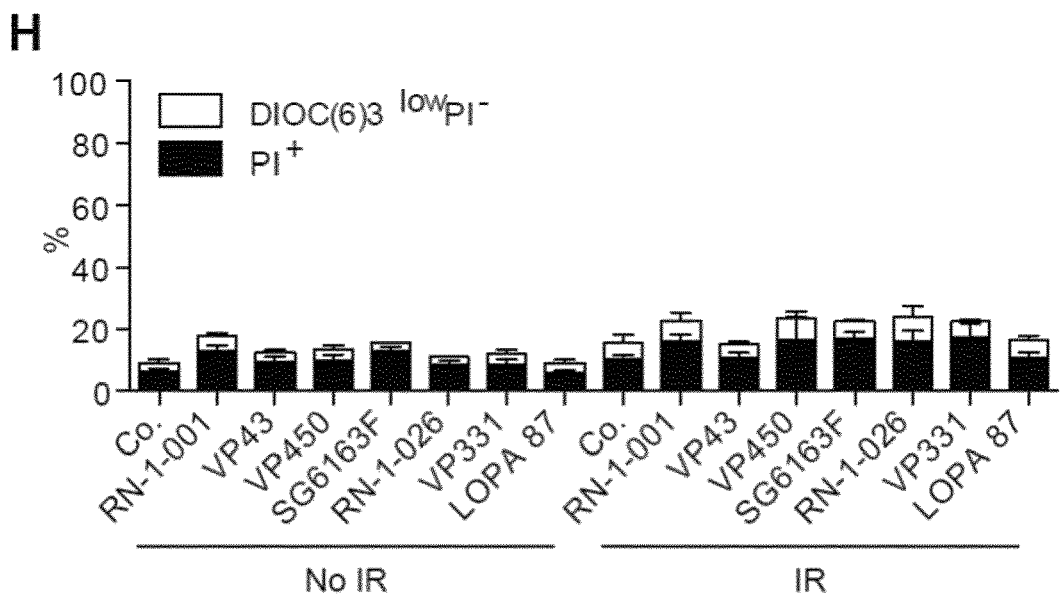
Figure 4:
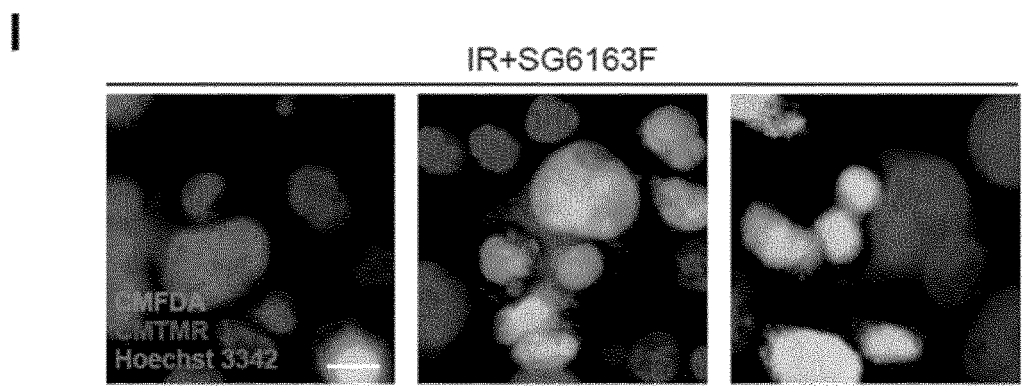
Figure 4:
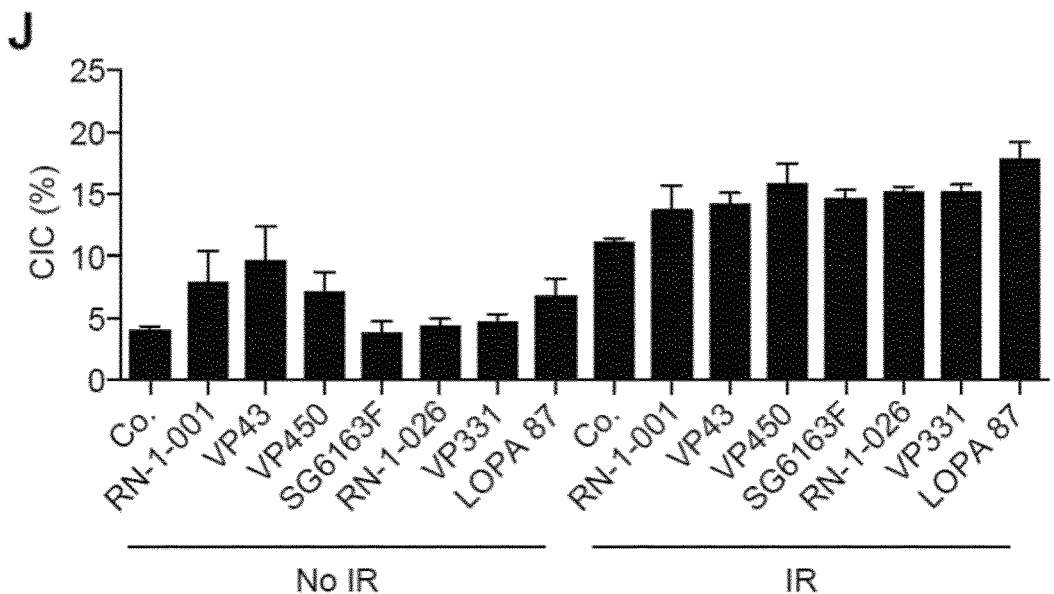

FIG. 4 Identification of cannibalism modulators triggered by ionizing radiation. Compounds from the Prestwick (A) and CEA (F) libraries were tested for their capacities to induce cellular cannibalism after ionizing radiation. Cannibal cells were detected after homotypic cultures of 8 gray γ-irradiation HCT116 cells in the presence or absence of 10 µM of the Prestwick (A) and CEA (E) library compounds. Each dot represents one compound. Representative images are shown in (B, G). (C, H) HCT116 cells were treated with the indicated drugs. After 24 h of treatment, cell death was monitored by staining with 3,3 dihexyloxacarbocyanine iodide ($DiOC_6(3)$) and PI+, and the percentage of dying ($DiOC_6(3)^{low}$ PI−, open bars) and dead ($DiOC_6(3)^{low}$ PI+, closed bars) cells was determined by cytofluorometry. Validation of the cannibalism inducers by fluorescent microscopy. Representative images (D, I) and quantification (E, J) are shown. Results are means s.e.m. of triplicate determinations.

Figure 5:
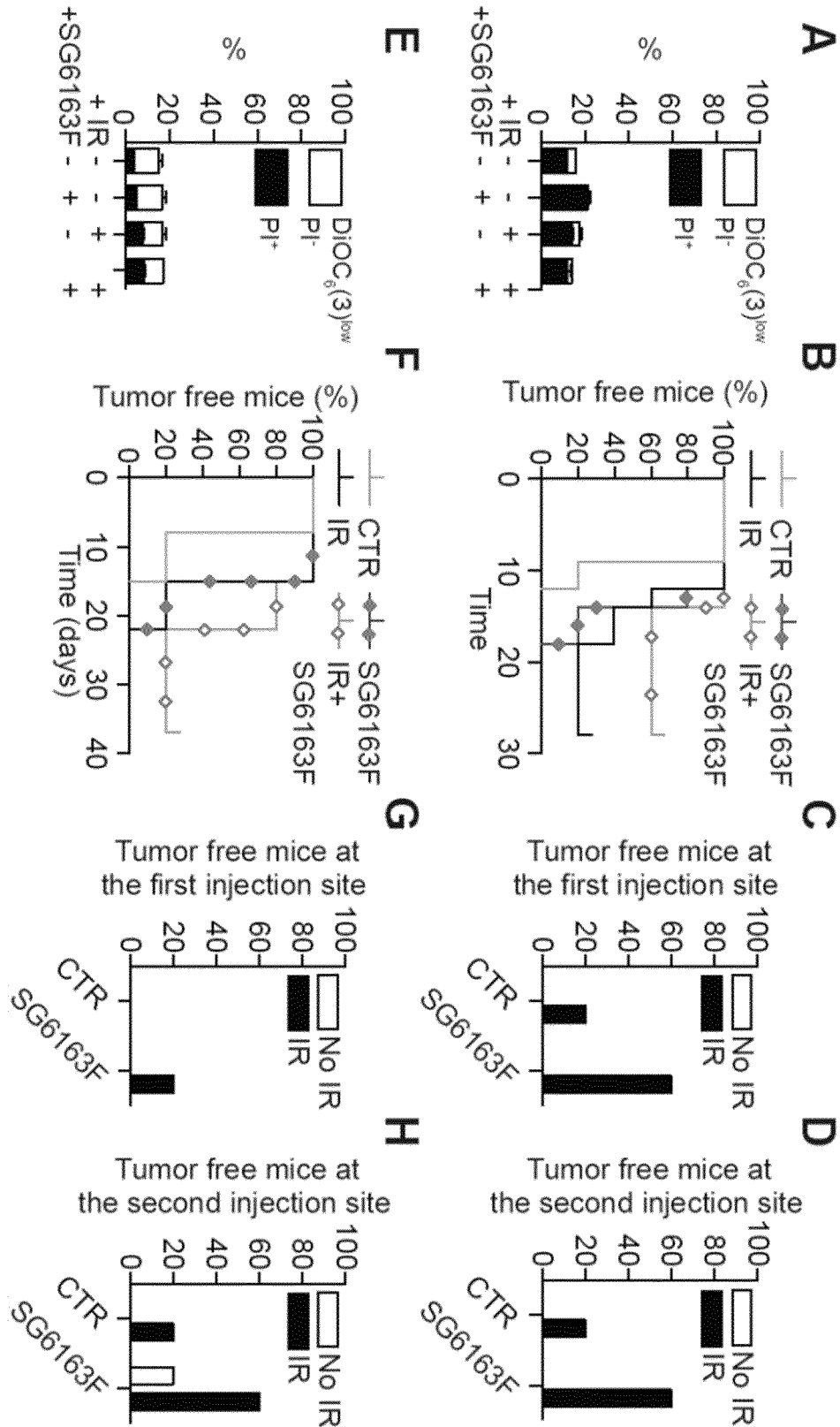
Figure 5:
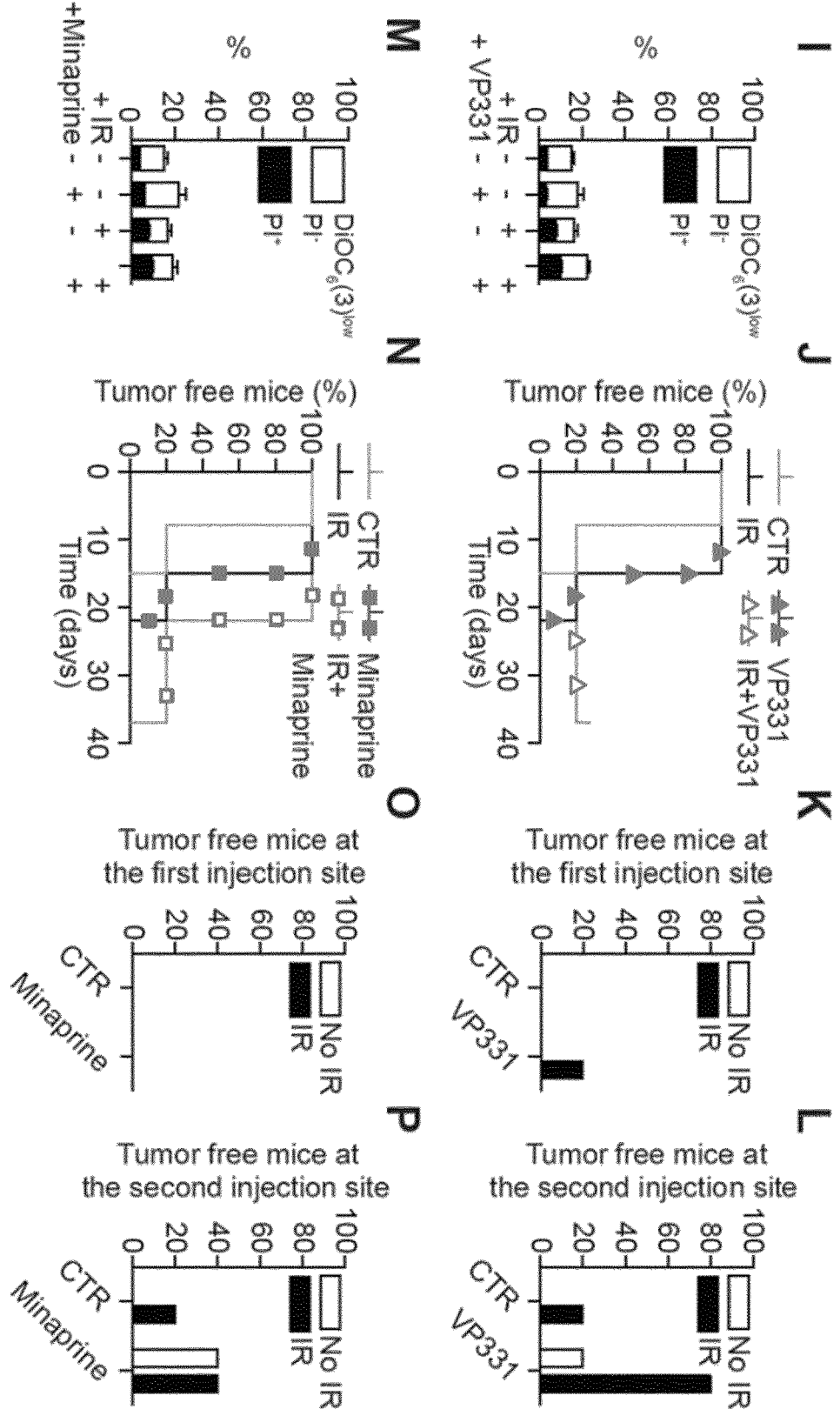
Figure 5:
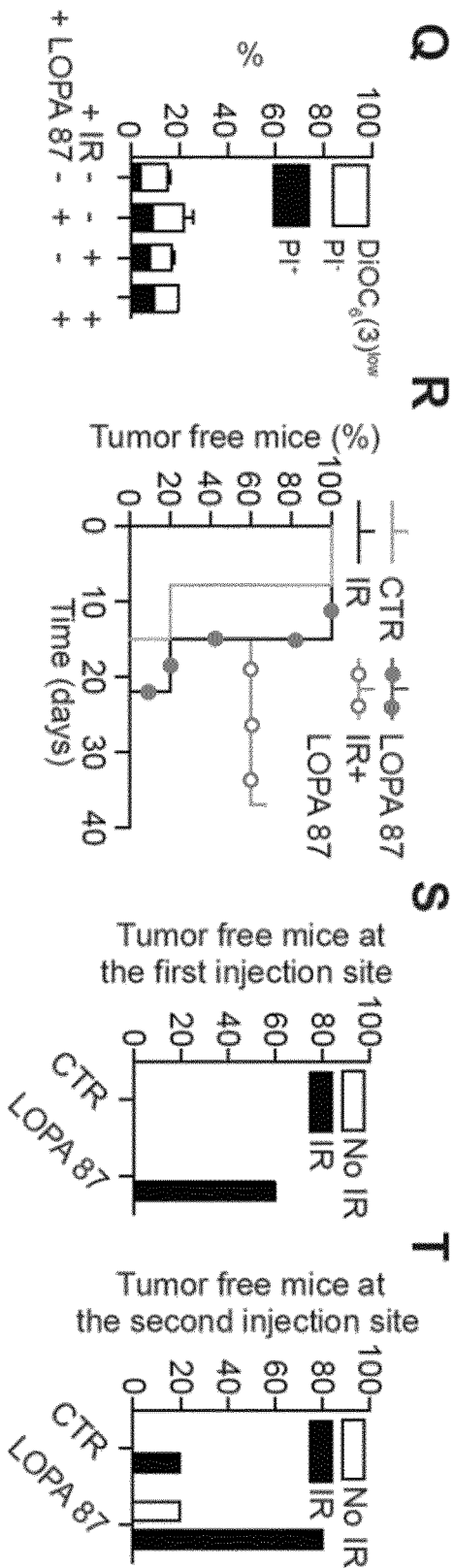

FIG. 5. Identification of cannibalism modulators as immunogenic cell death inducers. MCA205 (A) or CT26 (E, I, M, Q) cells were treated with the indicated drugs. After 24 h of coculture with the indicated treatment, cell death was monitored by staining $DiOC_6(3)$ and PI, and the percentage of dying ($DiOC_6(3)^{low}$ PI−, open bars) and dead ($DiOC_6(3)^{low}$ PI+, closed bars) cells was determined by cytofluorometry. (B-D) MCA205 cells or (F-H, J-L, N-P, R-T) CT26 cells cocultured after x irradiation with the indicated compounds were inoculated subcutaneously into the right flank of C56BL/6 or BALB/c mice, respectively. Seven days later, the mice were rechallenged with live cells injected into the opposite flank, and tumor growth was monitored (five mice per group).

FIG. 6. Tumor vaccination experiments. CT26 cells were treated for 24 hours with 10 µM VP331 (A, F, K), 10 µM Minaprine (B, G, L), 10 µM Lopa87 (C, H, M), 10 µM SG6163F (D, I, N), 10 µM Azaguanine-8 (8-aza) (E, J, O) alone or combined with 8 Gy ionizing radiation and inoculated (s.c.) into immunocompetent BALB/c mice, which were rechallenged at the opposite flank 7 days later with the same cancer cells. The percentage of tumor-free mice was evaluated three times a week for the following 38 days. Percentage of total tumor free mice (A-E), tumor free-mice at the first injection site (F to J, P) or at the second injection site (K to O, Q) are shown. (*P<0.05, P<0.01, *P<0.001, two-way ANOVA).

FIG. 7. Minaprine reduces tumor growth in immunocompetent mice after intratumoral or intraperitoneal injections. (A-C) 3 $10^6$ CT26 cells were implanted in immunocompetent BALB/c mice. Palpable tumors were injected with 10 µM Minaprine (or control) after 6 days. The tumor growth volume was then determined three times a week for the following 38 days (A and B). The percentage of mice survival was also determined (C). (D-I) 5 $10^5$ CT26 cells were implanted in immunocompetent BALB/c mice. After 12 days, tumor bearing mice were intraperitoneally injected with control (D and I), 0.3 mg/kg (E and I), 1 mg/kg (F and I), 3 mg/kg (G and I) or 10 mg/kg (H and I) of Minaprine. Tumor growth volumes (A-J) and fold change in the tumor volumes after intraperitoneal injection (D-I) were analyzed. Tumor growth volumes were the determined three times a week for the following 38 days.

EXAMPLES

I. Material and Methods
Chemicals, Cell Lines and Culture Conditions

Unless otherwise indicated, chemicals were purchased from Sigma-Aldrich. Antibiotics, media, supplements for cell culture were obtained from Life Technologies. Benzyloxycarbonyl-Val-Ala-Asp(OMe)-fluoromethylketone (Z-VAD-fmk) was from Bachem and recombinant mouse TNF-alpha from R&D systems. Human colon carcinoma HCT116 cells were cultured in McCoy's 5A medium and murine fibrosarcoma cell line L929 in Dulbecco's modified Eagle's medium. All the media were supplemented with 10% heat-inactivated fetal bovine serum (FBS), 10 mM HEPES buffers, 2 mM L-glutamine, 10 U/mL penicillin sodium and 10 g/mL streptomycin sulfate.

Irradiation

Cells were seeded in 6-well plates, 12-well plates or 25 cm² flasks and irradiated at indicated dose with gamma-ray irradiator IBL-637 ($Cs^{137}$, 1 Gy/min, gamma CIS-BioInternational, IBA, Saclay, France).

CellTracker™ Fluorescent Probes Labeling

Upon the removal of the culture medium, HCT116 cells were incubated with pre-warmed medium containing 10 µM of 5-chloromethylfluorescein diacetate (CMFDA, green fluorescence) or 5-(and-6)-(((4-Chloromethyl)Benzoyl)Amino)Tetramethylrhodamine (CMTMR, red fluorescence) (Molecular Probes-Life Technologie) for 45 min at 37° C. Thereafter, HCT116 cells were rinsed twice with pre-warmed medium, and incubated for 1 hour at 37° C. Stained cells were treated as indicated and cultured for cell death profiling analysis.

Cell Death Profiling by Quantitative Flow Imaging

Untreated HCT116 cells were labeled with CMFDA (green fluorescence, CMFDA+) or CMTMR, (red fluorescence, CMTMR) and treated HCT116 cells with CMFDA (green fluorescence, CMFDA+). The following cell mixtures were performed: untreated CMTMR+ HCT116 cells were mixed with untreated CMFDA+ HCT116 cells, or untreated CMTMR+ HCT116 cells were mixed with treated CMFDA+ HCT116 cells. Then, cells were co-cultured during 24 hours in the presence or absence of the pharmacological inhibitor of ROCK, Y27632 (30 µM), the pan-caspase inhibitor, Z-VAD-fmk (ZVAD, 100 µM), the inhibitor of caspase-1, Ac-YVAD-cmk (YVAD, 100 µM), the necroptosis inhibitor, Necrostatin-1 (NEC1, 30 µM), the inhibitor of the vacuolar type H(+)-ATPase (V-ATPase) inhibiting autophagy, Bafilomycin A1 (BafA1, 50 nM), the inhibitor of Cdks with an anti-mitotic activity, Roscovitine (Rosco, 10 µM). After 24 hours of co-culture, both detached and adherent cells were collected and stained with Hoechst 33345 (10 µg/mL) during 1 hour at 37° C. in warmed complete medium. To detect phosphatidylserine (PS) exposure and plasma membrane permeability, labeled HCT116 cells were successively incubated with Biotin-AnnexinV (BD Pharmingen) as recommended by manufacturer, 0.5 g BV786-Streptavidin (BD Biosciences) and 3 µM DRAQ7 (BioStatus) during 15 minutes at 25° C. After washing with PBS solution, samples were immediately analyzed using an imaging flow cytometer FlowSight® (Amnis®, part of EMD Millipore). Data were acquired at a 20× magnification, using INSPIRE software. The 405 nm, 488 nm, and 561 nm lasers were used for excitation. Brightfield, Annexin V-BV786, DRAQ7, CMFDA, CMTMR and Hoechst 33345 stainings were detected using respectively channels for 420-480 nm, 745-800 nm, 642-745 nm, 480-560 nm, 595-642 nm and 430-505 nm. At least 1000 events of cells per sample were analyzed. Additional single-labeled controls were prepared to normalize fluorescent signal across different channels. Acquired data were analyzed using the IDEAS analysis software (v6.1; Merck-Millipore). Gating strategy was the following. Cells were gated for focused cells using the Gradient RMS feature. Cells were gated for single cells using the aspect ratio and area features. For the cannibalism detection, cells were gated in the double positive CMFDA$^+$ and CMTMR$^+$ staining.

Flow Cytometry and Confocal Fluorescent Microscopy

To detect PS exposure, plasma membrane permeability and cell cycle progression, cells were after co-culture sequentially labeled with specific fluorescent probes (such as FITC-conjugated AnnexinV, propidium iodide, and Hoechst 33342) and analyzed by flow cytometry. Both detached and adherent cells were collected and stained with Hoechst 33345 (10 µg/ml) during 1 hour at 37° C. in warmed complete medium. After washing with PBS, HCT116 cells were suspended in 1× binding buffer supplemented with fluorescein isothiocyanate (FITC)-conjugated Annexin V (BD Biosciences) and propidium iodide (PI, 1 µg/mL) (Sigma), as per manufacturer's instructions. Samples were then analyzed using LSRII flow cytometer (Becton Dickinson) and the FlowJo software v10. For confocal fluorescence microscopy, HCT116 cells were fixed after co-culture in 3.7% paraformaldehyde-PBS for 15 minutes and counterstained with 1 µg/mL Hoechst 33342 (Invitrogen) for 15 minutes. Then, cells were analyzed by confocal SPE microscope equipped with Apochromat 63×1.3 NA and 63×1.15 NA oil immersion objectives. The Leica Aplication Suite (LAS) software was used (Leica Microsystems).

Western Blots

Total cellular proteins were extracted in lysis buffer (containing 1% NP40, 20 mmol/L HEPES, 10 mmol/L KCl, 1 mmol/L EDTA, 10% glycerol, protease and phosphatase inhibitor tablets). Protein extracts (30 µg) were run on 4-12% NuPAGE® Novex® Bis-Tris gels (Life Technologies) and transferred at 4° C. onto Immobilon polyvinylidifluoride (PVDF) membranes (Thermo Scientific). After blocking, membranes were incubated at 4° C. overnight with primary antibodies specific for: caspase-3 (#9662), cleaved caspase-3 (Asp175) (#9661), Myosin Light Chain 2 (MLC2) (#3672), phospho-MLC2 (Ser19) (#3675), LC3 A/B (#4108), p-(S)-CDKs Substrate (#9477) were obtained from Cell Signaling Technology. Antibodies against GAPDH (#MAB374) were purchased from Millipore. Horseradish peroxidase-conjugated goat anti-mouse or anti-rabbit (Southern Biotechnology) antibodies were then incubated during 1 h and revealed with the SuperSignal West Pico® reagent (Thermo Fisher Scientific) or the ECL™ Prime Western Blotting Detection System (GE Healthcare) using an ImageQuant LAS 4000 software-assisted imager (GE Healthcare).

Statistical Analyses

Each experiment has been repeated at least three times, yielding comparable results.

Unless otherwise indicated, figures illustrate quantitative data from one representative experiment (means±SEM, n=3). Data were analyzed by means of Prism v. 5.03 (GraphPad Software, La Jolla, Calif., USA). Statistical significance was assessed by two-tailed Student's t tests. In all experiments, p values <0.05 were considered as statistically significant.

II. Results

Cell death profiling analysis using multispectral imaging flow-cytometry allows the simultaneous detection of non-cell autonomous and cell autonomous death modalities. The ability of cells to die through NCA processes led us to reconsider from a conceptual point of view our methodological approach to consider cell death processes. Indeed, the choice of the morphological and/or biochemical parameters to be considered as well as the technological approach to be used to detect cell death predefines in advance the results to be expected and does not allow or very rarely to identify new lethal processes such as cellular cannibalism or entosis. The field of radiotherapy is also facing this problem. Indeed, it has been revealed in separate studies that irradiation can trigger many lethal processes such as apoptosis, autophagic cell death, necrosis or mitotic death[35,36]. It has recently been shown in separate studies that irradiation of the same cell type with the same doses could trigger apoptosis[37], but also mitotic death[38]. In previous studies it was revealed that the onset of apoptosis and mitotic death observed very rapidly following irradiation do not correlate with clonogenic survival observed in the longer term[35]. These studies highlighted the existence of unknown lethal processes involved in the elimination of irradiated cells. Moreover, the increasing number of publications revealing the influence of cellular cannibalism and entosis in the control of tumor growth and in the elimination of metastatic cells urges one to follow the onset of this process of NCAD. Considering the diversity of lethal stimuli that can potentially initiate both non-cell autonomous and cell autonomous cell death modalities and the complexity of signaling pathways (involving (or not) caspases, cathepsins or granzymes) that control both processes, it was decided to simultaneously detect non-cell autonomous and cell autonomous death modalities elicited by IR. To determine whether after lethal insults a cellular population may undergo simultaneously direct or/and by-stander-cell killing that may be executed in a cell-autonomous or non-cell autonomous manner, a cell death profiling analysis was designed based on the co-culture of HCT116 cells that have been labeled with 5-chloromethylfluorescein diacetate (CMFDA, green) fluorescent vital probe and treated by ionizing radiations (γ-rays) with isogenic HCT116 cells that have been labeled with 5-(and-6)-(((4-chloromethyl)benzoyl)amino) tetramethylrhodamine (CMTMR, red) fluorescent vital probe. After 24 hours of co-culture, treated CMFDA$^+$ cells, untreated CMTMR$^+$ cells and the total (CMFDA$^+$ cells and CMTMR$^+$ cells) cell population were analyzed for phosphatidyl serine (PS) exposure, loss of plasma membrane integrity and DNA content to simultaneously detect cell death induction of both treated cells and (untreated) neighboring cells. To characterize molecular mechanisms involved in the execution of detected cell death modalities, co-cultures were performed in presence cell death modulators (such as ROCK1 inhibitor (Y27632), pan-caspase inhibitor (ZVAD-fmk), caspase-1 inhibitor (YVAD-fmk), necrostatin (NEC1), bafilomycine A1 (BafA1) and Roscovitine (Rosco)) that are respectively known to inhibit cell engulfment (a process that initiates entosis[16], emperiptosis[17] and cellular cannibalism[16]), proteolytic cleavage of caspase-3 or caspase-7 (which contributes to the execution of apoptosis[39], mitotic death[38, 40] or emperiposis[17]) or of caspase-1 (which is required for pyroptosis[41]), the activation of the pro-necroptotic kinase RIP1 kinase (RIPK1) which contributes to necroptosis[42], the fusion between autophagosomes and lysosomes impairing thus the maturation of autophagic vacuoles during autophagy and autophagy-associated cell death[43]) and finally, the cyclin-dependent kinase 1 (Cdk1)-Cyclin B activity and the progression through mitosis which is required for mitosis associated deaths such mitotic death[40, 44]. The simultaneous detection of the PS exposure, loss of plasma membrane integrity, DNA content of cellular partners combined with pharmacological inhibition of cell death modulators allowed us to detect during co-cultures through the use of multispectral imaging flow-cytometry the execution of at least 9 cell death modalities (including apoptosis, mitotic death, pyroptosis, autophagic cell death, necrosis, necroptosis, entosis, emperitosis and cellular cannibalism) on targeted cells and on neighboring cells (FIG. 1, A-B), thus discriminating non cell-autonomous deaths from cell autonomous deaths and direct cell killings from bystander lethal effects. This methodology allowed one to define the cell death profiling elicited by IR.

Ionizing radiation-elicited cell death profiling highlights the induction of cell death on both irradiated and non-irradiated cancer cells. Despite the intensive biological and pharmaceutical research implemented to better characterize cellular and biochemical processes associated with anticancer treatments, lethal mechanisms responsible for the therapeutic effects of radiotherapy, which is one of the most frequent anticancer treatment used in clinic, are still unknown. Lethal processes (such as apoptosis and mitotic catastrophe) that have been detected in response to ionizing radiation were not directly implicated in treatment efficiency[35], suggesting that additional cell death modalities that are still unknown may contribute to therapeutic effects of radiotherapy. In this context was determined the cell death profiling of irradiated cancer cells. According to the above described methodology, CMFDA-labeled cells were irradiated or not with 4 grays, mixed after 24 hours together at a 1:1 ratio with CMTMR-labeled cells, and cultured for 24 hours in presence of each indicated inhibitors (Supplementary FIGS. 1A-1E). Then, PS exposure, the membrane integrity and DNA content of each cellular partner were respectively determined using AnnexinV-BV786, DRAQ7 and Hoechst 33342 stainings. Despite no significant increase of apoptotic and necrotic cell deaths (as revealed by the analysis of AnnexinV$^+$DRAQ7$^-$ and DRAQ7$^+$ cells) was observed on neighboring cell population (CMTMR$^+$ cells) (FIGS. 2A, 2B and 2D) and on untreated control cell population (FIGS. 2A, 2D and 2E), a significant increase of these both types of death on total cell population (as revealed by considering CMFDA$^+$ and CMTMR$^+$ cell population) (FIGS. 2A-2C) and on irradiated cell population (CMFDA$^+$ cells) (FIGS. 2B and 2E) was detected after 24-hours of co-culture, demonstrating that the present methodology allows to detect cell death modalities of both non irradiated and irradiated cells. It was also observed that the pan-caspase inhibitor Z-VAD-fmk and pharmacological cyclin-dependent kinase inhibitor roscovitine (Rosco) inhibited the exposure of PS on the outer plasma membrane of irradiated CMFDA$^+$ cells (FIG. 2E), confirming as previously published[45, 46] that irradiated CMFDA$^+$ cells require both caspase activation and progression through mitosis to die. In addition, the impairment of autophagic flux with bafilomycin A1 (BafA1) increased the frequency of dying cells (AnnexinV$^+$DRAQ7$^-$ and DRAQ7$^+$ cells) in the total cell population (CMFDA$^+$ and CMTMR$^+$ cells) (FIG. 2C), in non-irradiated CMTMR$^+$ cells (FIG. 2D) and in irradiated CMFDA$^+$ cells (FIG. 2E), thus revealing that autophagy is a survival cellular mechanism elicited by ionizing radiation that contributes to rescue both non-irradiated and irradiated cells from death. In addition, the simultaneous analysis of the progression of treated and untreated cells through their cell cycles showed that cell death inductions are associated with the escapement of irradiated CMFDA$^+$ cells from G1 arrest and led to their accumulations in S and G2/M phases (FIGS. 2F, 2G and 2J). No alteration of cell cycle is detected on total or CMTMR$^+$ cell populations, underlining that the cell cycle alterations are only detected on irradiated cells (FIGS. 2F, 2G and 2I). These results, which were also confirmed by classical flow-cytometry analysis (Supplementary FIGS. 2A-2B), demonstrated that after ionizing radiation, both irradiated and non-irradiated cancer cells undergo caspase-1 dependent cell death. Altogether, these results highlighted the ability anticancer agents to simultaneously eliminate cancer cells through direct cell killing and bystander effects.

Ionizing radiation-elicited cell death profiling also reveals the induction of non-cell-autonomous death modalities. In parallel, in the same co-culture was determined the ability of irradiated CMFDA$^+$ cells to engulf or to invade neighboring cells, two cellular processes required for the induction cellular cannibalism-associated cell deaths (such as cellular cannibalism, emperitosis or phagoptosis) or cell-in-cell invasion-elicited cell deaths (such as entosis). Multispectral imaging flow-cytometry analysis revealed that gamma-irradiated CMFDA$^+$ cells triggered the engulfment of neighboring cells (as revealed by the internalization of "target" CMTMR$^+$ cells by gamma-irradiated CMFDA$^+$ cells (FIGS. 3A and 3B)). This process that was not affected by the pan-caspase inhibitor Z-VAD-fmk is repressed by the inhibitor of ROCK1 (Y27632) (FIG. 3B), thus revealing that the detected cell-in-cell internalization is distinct from phagocytic uptake of apoptotic cells and requires ROCK1 activity to occur. Cannibalistic activity of gamma-irradiated cells was also confirmed by confocal microscopy (FIG. 3D-3F). Interestingly, cell death profiling analysis also allowed to distinguish live cell engulfment from the phagocytosis of apoptotic CMFDA$^+$ cells by lived CMTMR$^+$ cells that is consecutive to the induction of apoptosis by the treatment with bafylomycin A1 (FIG. 3B). Then, the cell fates of engulfed CMTMR$^+$ cells and irradiated engulfing CMFDA$^+$ cells were evaluated. It was observed that almost all engulfed CMTMR$^+$ cells exhibited signs of cellular degradation (as revealed by the DNA content loss of internalized cells detected with multispectral imaging flow-cytometry (FIG. 3A) and confocal microscopy (FIGS. 3D and 3E)). This process is significantly reduced in presence of the pan-caspase inhibitor Z-VAD-fmk and the caspase-1 inhibitor YVAD-fik, revealing that IR-mediated death of engulfed cells requires caspases to occur and may be executed through caspase-1 dependent apoptosis, that is also known as pyroptosis. In addition, it was also revealed that 90% of cannibal cells did not expose PS or exhibit loss of the integrity of their plasma membrane (Supplementary FIG. 2C) underlining that after IR-mediated cell engulfment, the internalized cells are precipitated to death without modulating the viability of cannibal cells. Altogether, these results demonstrated that ionizing radiation simultaneously eliminates cancer cells through combined effects of direct cell killing, bystander lethal effect and cellular cannibalism-associated cell death. These results highlight the urgent need to simultaneously measure the induction of non-cell autonomous and cell autonomous death subroutines during lethal processes.

Chemical library screening leads to the identification of IR-mediated cellular cannibalism enhancers. Then, the screening of a library of chemical compounds was developed in order to identify compounds able to induce IR-mediated cellular cannibalism. Thus, HCT116 cells that have been treated with a radiation dose of 8 Gray were stained either with orange CMTMR cell tracker or green CMFDA cell tracker and cultivated in presence of 10 µM of chemical compounds. After 24 hours of culture, cells have been stained with nuclear dye (5 µg/ml of Hoechst 33342 during 1 h at 37° C.) and analyzed using the FlowSight® Imaging Flow Cytometer for cellular cannibalism. Each of these compounds were classified according to their Z-score 47 and identified respectively 13 and 11 candidate compounds (FIGS. 4A, 4B, 4F and 4G). Then, the identified compounds were validated by combining flow cytometry approaches (in order to eliminate cytotoxic compounds by simultaneously monitoring the depolarization of the internal mitochondrial membrane and the plasma membrane permeability of the treated cells) with confocal microscopy approaches (to confirm the modulation of IR-induced cellular cannibalism by candidate compounds) (FIGS. 4C-E and 4H-J). After the completion of three independent experiments, chemical compounds with no effect (such as Fenbendazol or Carbimazole) or exhibiting high cytotoxicity (such as RN-1-183) have been eliminated. Finally, 16 chemical compounds that are able to enhance the capacity of IR to trigger cellular cannibalism were identified (FIGS. 4E and 4J, Tables 1&2).

The combination of IRCCE with IR induces efficient antitumor immunity. Considering that immunogenic cell death (ICD) inducers were identified (such as Digoxin, Digitoxin, Lanatoside C or Doxorubicin hydrochloride)[3, 4, 48-51]) as IRCCE, the ability of these compounds to induce an antitumor immunity after radiotherapy was evaluated. First, a preclinical approaches was developed to study the immunological effects of IRCCE on two mouse models of carcinoma (colon CT26 carcinoma and fibrosarcoma MCA205). Initially, the ability of the combination of IRCCE+IR to trigger a specific anti-tumor immune response was appreciated using immunocompetent mice through anti-tumor vaccination assays. According to previously published studies[52], the injection of cancer cells succumbing to an immunogenic cell death (ICD) into immunocompetent mice must elicit a protective immune response that is specific for tumor antigens. Thus, $3 \times 10^5$ MCA205 cells were first treated with 10 µM of SG6163F for 24 hours. Then, treated cells were inoculated subcutaneously in 200 µl PBS into the lower flank of 8-week-old female C57BL/6 mice. One week later, $3 \times 10^4$ untreated control cells were inoculated into the contralateral flank of mice. Tumors were evaluated weekly using a common caliper. Animals bearing tumors that exceeded 20-25% body mass were euthanatized. It was observed that mice treated with IR or SG6163F alone are not able to induce a significant increase of cell death in vitro (FIG. 5A). In fact, they did not exhibit a protective response after the inoculation of untreated cells, revealing that the dose of radiation and the concentration of SG6163F used were not sufficient to stimulate an anticancer immune response (FIG. 5B). These results were consistent with previously published results demonstrating that a protective response is only detected when cancer cells were exposed to cytotoxic anticancer treatment in vitro until 70% of the cells expose phosphatidylserine on the outer leaflet of the plasma membrane 48. Surprisingly, it was observed that the combined treatment of MCA205 cells with 8 Gy of IR and 10 µM of SG6163F induced a protective response in 3 of 5 mice that have been injected (FIG. 5B). These results revealed for the first time that the combination of IRCCE+IR may elicit an IR-mediated anticancer immune response in absence of a significant increase of death of treated and irradiated cells (FIG. 5A), suggesting that cellular cannibalism or cellular cannibalism-associated signaling pathways may contribute to the induction of tumor immunogenicity. Then, $3 \times 10^6$ CT26 cells were irradiated with 8 Gy in presence of 10 µM of SG6163F (FIGS. 5E and 5F), VP331 (FIGS. 5I and 5J), Minaprine dihydrochloride (FIGS. 5M and 5N) or LOPA87 (FIGS. 5Q and 5R) for 24 hours. Then, cells were inoculated as previously described subcutaneously in 200 PBS into the lower flank of 8-week-old female BALB/c mice. One week later, $5 \times 10^5$ untreated control cells were inoculated into the contralateral flank of mice and tumors were evaluated weekly using a common caliper. As previously mentioned, animals bearing tumors that exceeded 20-25% body mass were euthanatized. The percentage of dying cells in each condition was evaluated by determining with DiOC(6)3/IP staining (FIGS. 5E, 5I, 5M and 5Q). Finally, the ability of these compounds to repress the growth of cancer cells that have been injected 7 days after injection of irradiated and treated cancer cells was appreciated. It was observed a significant increase in the frequency of mice showing a protective response after injection of cancer cells that have been treated with IR and chemical compounds (FIGS. 5H, 5L, 5P and 5T).

A second anti-tumor vaccination assay was done on CT26 mouse models of carcinoma as previously described. Briefly, CT26 cells were irradiated with 8 Gy in presence of 10 µM of VP331 (FIG. 6A, 6F, 6K), Minaprine dihydrochloride (FIG. 6B, 6G, 6L), LOPA87 (FIG. 6C, 6H, 6M), SG6163F (FIG. 6D, 6, 6N), or Azaguanine-8 (8-aza) (FIG. 6E, 6J, 6O) for 24 hours. Then, cells were inoculated as previously described into immunocompetent BALB/c mice. Finally, the ability of these compounds to repress the growth of cancer cells that have been injected 7 days after injection of irradiated and treated cancer cells was appreciated. The previous results were confirmed. Significant increases in the frequency of mice showing a protective response after injection of cancer cells that have been treated with IR and chemical compounds was observed (FIGS. 6P and 6Q). Interestingly, minaprine dihydrochloride (FIGS. 6B, 6G, 6L, 6P and 6Q) and azaguanine-8 (FIGS. 6E, 6J, 6O, 6P and 6Q) alone induce an increase of protective response after injection of cancer cells.

Altogether, these results revealed the ability of chemical compounds identified with the present platform to induce a protective anticancer immune response.

Confirmation of the Anti-Tumoral Effect of Minaprine Dihydrochloride on its Own

We previously revealed that Minaprine favors the induction of Type IV cell death modality, also known as cellular cannibalism. This non-cell-autonomous death, which is detected when cancer cells are treated with Minaprine, is significantly increased in presence of ionizing radiation (IR), thus revealing the ability of Minaprine to enhance the non-cell-autonomous cancer cell killing elicited in response to conventional anticancer treatments (such as radiotherapy).

Minaprine also exhibits immunogenic properties and stimulate specific antitumor immune response in vivo as revealed by antitumor vaccination assays (see above).

To further characterize the immunomodulatory effects of Minaprine, we studied the impact of intratumoral and intraperitoneal injection of Minaprine on the growth of mouse cancer cells.

Material and Methods

Chemicals, Cell Lines and Culture Conditions.

Minaprine was obtained from Jean-Christophe Cintrat. CT26 tumor cells were cultured in RPMI medium supplemented with 10% heat-inactivated fetal bovine serum (FBS), 10 mM HEPES buffers, 2 mM L-glutamine, 10 U/mL penicillin sodium and 10 µg/mL streptomycin sulfate.

Tumor Growth in Immunocompetent Mice.

For intratumoral injection, $3 \cdot 10^6$ Balb/c-derived CT26 tumor cells were subcutaneously implanted in 8 week-old Balb/c mice (Janvier Laboratories). After 6 days, 10 µM of Minaprine or control phosphate buffer saline (PBS) was injected into tumors (20 µl) and tumor volume was evaluated 3 times a week. For intraperitoneal injection, $5 \cdot 10^5$ Balb/c-derived CT26 tumor cells were subcutaneously implanted in 8 week-old Balb/c mice (Janvier Laboratories). After 12 days, tumor-bearing mice were intraperitonealy injected with different concentrations of Minaprine (0.3, 1, 3 and 10 mg/kg) or PBS. Tumor volume was also evaluated 3 times a week. The experiments were randomized, performed in compliance with the EU Directive 63/2010 and approved by Ethical Committee at Gustave Roussy Cancer Campus (CEEA IRCIV/IGR n°26).

Statistics and Reproducibility.

No statistical methods or criteria were used to estimate sample size or to include/exclude samples. The investigators were not blinded to group allocation during experiments and outcome assessment. Results are expressed as mean value SEM. To determine statistical significance, Two-way ANOVA (FIG. 7A) and Log rank (Mantel-Cox) (FIG. 7I) tests were used for calculation of P values. Prism 6 Software was used for the generation of survival graphs and statistical significance. Statistical significance was given as **p value<0.01 or *p value<0.05.

Results

We first subcutaneously implanted $3 \cdot 10^6$ Balb/c-derived CT26 colon cancer cells in immunocompetent Balb/c mice. After 6 days, tumor-bearing mouse were randomized and 10 µM of Minaprine (3 mg/kg) was injected into tumors. Tumor growth was analyzed during 38 days. Interestingly, we observed that the intratumoral injection of 3 mg/kg of Minaprine significantly decreases the growth of tumors (FIGS. 7A and 7B). This process is associated with the increase survival of treated mice as compared to untreated control mice (FIG. 7C), thus revealing the ability of intratumoral injection of Minaprine to reduce tumor growth.

We next determined whether intraperitoneal injections of Minaprine could also impact tumor growth. Thus, $5 \cdot 10^5$ Balb/c-derived CT26 cells were implanted into immunocompetent Balb/c mice. After 12 days, tumor-bearing mice were randomized, intraperitoneally injected with control (FIGS. 7D and 7I) or with Minaprine at different concentrations (FIGS. 7E-7I). As observed with the intratumoral injection of Minaprine, we observed that intraperitoneal injection of 1 mg/kg, 3 mg/kg and 10 mg/kg of Minaprine significantly decreased the growth of treated tumors as compared to control (FIGS. 7D and 7I) or tumors treated with 0.3 mg/kg Minaprine (FIGS. 7E and 7I), indicating that the intratumoral injection of Minaprine also impact tumor growth.

Altogether, these results highlight the ability of both intratumoral and intraperitoneal injections of Minaprine to reduce tumor growth.

BIBLIOGRAPHIC REFERENCES

1 Tobias J S. Clinical practice of radiotherapy. *Lancet* 1992; 339:159-163.
2 Apetoh L, Ghiringhelli F, Tesniere A et al. The interaction between HMGB1 and TLR4 dictates the outcome of anticancer chemotherapy and radiotherapy. *Immunol Rev* 2007; 220:47-59.
3 Apetoh L, Ghiringhelli F, Tesniere A et al. Toll-like receptor 4-dependent contribution of the immune system to anticancer chemotherapy and radiotherapy. *Nature medicine* 2007; 13:1050-1059.
4 Ghiringhelli F, Apetoh L, Tesniere A et al. Activation of the NLRP3 inflammasome in dendritic cells induces IL-1beta-dependent adaptive immunity against tumors. *Nature medicine* 2009; 15:1170-1178.
5 Michaud M, Martins I, Sukkurwala A Q et al. Autophagy-dependent anticancer immune responses induced by chemotherapeutic agents in mice. *Science* 2011; 334:1573-1577.
6 Kingsley D P. An interesting case of possible abscopal effect in malignant melanoma. The British journal of radiology 1975; 48:863-866.
7 Ohba K, Omagari K, Nakamura T et al. Abscopal regression of hepatocellular carcinoma after radiotherapy for bone metastasis. *Gut* 1998; 43:575-577.
8 Postow M A, Callahan M K, Barker C A et al. Immunologic correlates of the abscopal effect in a patient with melanoma. *The New England journal of medicine* 2012; 366:925-931.
9 Rees G J, Ross C M. Abscopal regression following radiotherapy for adenocarcinoma. *The British journal of radiology* 1983; 56:63-66.
10 Demaria S, Ng B, Devitt M L et al. Ionizing radiation inhibition of distant untreated tumors (abscopal effect) is immune mediated. *International journal of radiation oncology, biology, physics* 2004; 58:862-870.
11 Meng Y, Beckett M A, Liang H et al. Blockade of tumor necrosis factor alpha signaling in tumor-associated macrophages as a radiosensitizing strategy. *Cancer research* 2010; 70:1534-1543.
12 Dewan M Z, Galloway A E, Kawashima N et al. Fractionated but not single-dose radiotherapy induces an immune-mediated abscopal effect when combined with anti-CTLA-4 antibody. *Clinical cancer research: an official journal of the American Association for Cancer Research* 2009; 15:5379-5388.
13 Kroemer G, Galluzzi L, Vandenabeele P et al. Classification of cell death: recommendations of the Nomenclature Committee on Cell Death 2009. *Cell death and differentiation* 2009; 16:3-11.
14 Vanden Berghe T, Vanlangenakker N, Parthoens E et al. Necroptosis, necrosis and secondary necrosis converge on similar cellular disintegration features. *Cell death and differentiation* 2010; 17:922-930.

15 Aaes T L, Kaczmarek A, Delvaeye T et al. Vaccination with Necroptotic Cancer Cells Induces Efficient Antitumor Immunity. *Cell reports* 2016; 15:274-287.

16 Overholtzer M, Mailleux A A, Mouneimne G et al. A nonapoptotic cell death process, entosis, that occurs by cell-in-cell invasion. *Cell* 2007; 131:966-979.

17 Wang S, He M F, Chen Y H et al. Rapid reuptake of granzyme B leads to emperitosis: an apoptotic cell-in-cell death of immune killer cells inside tumor cells. *Cell death & disease* 2013; 4:e856.

18 Brown G C, Neher J J. Eaten alive! Cell death by primary phagocytosis: 'phagoptosis'. *Trends in biochemical sciences* 2012; 37:325-332.

19 Brown G C, Vilalta A, Fricker M. Phagoptosis—Cell Death By Phagocytosis—Plays Central Roles in Physiology, Host Defense and Pathology. *Current molecular medicine* 2015; 15:842-851.

20 Sierro F, Tay S S, Warren A et al. Suicidal emperipolesis: a process leading to cell-in-cell structures, T cell clearance and immune homeostasis. *Current molecular medicine* 2015; 15:819-827.

21 Khandelwal S, van Rooijen N, Saxena R K. Reduced expression of CD47 during murine red blood cell (RBC) senescence and its role in RBC clearance from the circulation. *Transfusion* 2007; 47:1725-1732.

22 Lagasse E, Weissman I L. bcl-2 inhibits apoptosis of neutrophils but not their engulfient by macrophages. *The Journal of experimental medicine* 1994; 179:1047-1052.

23 Overholtzer M, Brugge J S. The cell biology of cell-in-cell structures. *Nat Rev Mol Cell Biol* 2008; 9:796-809.

24 Li Y, Sun X, Dey S K. Entosis allows timely elimination of the luminal epithelial barrier for embryo implantation. *Cell reports* 2015; 11:358-365.

25 Benseler V, Warren A, Vo M et al. Hepatocyte entry leads to degradation of autoreactive CD8 T cells. *Proc Natl Acad Sci USA* 2011; 108:16735-16740.

26 Ni C, Huang L, Chen Y et al. Implication of cell-in-cell structures in the transmission of HIV to epithelial cells. *Cell research* 2015; 25:1265-1268.

27 Ni C, Chen Y, Zeng M et al. In-cell infection: a novel pathway for Epstein-Barr virus infection mediated by cell-in-cell structures. *Cell research* 2015; 25:785-800.

28 Bartosh T J, Ullah M, Zeitouni S, Beaver J, Prockop D J. Cancer cells enter dormancy after cannibalizing mesenchymal stem/stromal cells (MSCs). *Proc Natl Acad Sci USA* 2016; 113:E6447-E6456.

29 Lugini L, Matarrese P, Tinari A et al. Cannibalism of live lymphocytes by human metastatic but not primary melanoma cells. *Cancer research* 2006; 66:3629-3638.

30 Wang S, Guo Z, Xia P et al. Internalization of N K cells into tumor cells requires ezrin and leads to programmed cell-in-cell death. *Cell research* 2009; 19:1350-1362.

31 He M F, Wang S, Wang Y, Wang X N. Modeling cell-in-cell structure into its biological significance. *Cell death & disease* 2013; 4:e630.

32 Sun Q, Cibas E S, Huang H, Hodgson L, Overholtzer M. Induction of entosis by epithelial cadherin expression. *Cell research* 2014; 24:1288-1298.

33 Cano C E, Sandi M J, Hamidi T et al. Homotypic cell cannibalism, a cell-death process regulated by the nuclear protein 1, opposes to metastasis in pancreatic cancer. *EMBO molecular medicine* 2012; 4:964-979.

34 Sun Q, Luo T, Ren Y et al. Competition between human cells by entosis. *Cell research* 2014; 24:1299-1310.

35 Abend M. Reasons to reconsider the significance of apoptosis for cancer therapy. *International journal of radiation biology* 2003; 79:927-941.

36 Gudkov A V, Komarova E A. The role of p53 in determining sensitivity to radiotherapy. *Nature reviews Cancer* 2003; 3:117-129.

37 Zhang P, Castedo M, Tao Y et al. Caspase independence of radio-induced cell death. *Oncogene* 2006; 25:7758-7770.

38 Castedo M, Perfettini J L, Roumier T, Andreau K, Medema R, Kroemer G. Cell death by mitotic catastrophe: a molecular definition. *Oncogene* 2004; 23:2825-2837.

39 Garcia-Calvo M, Peterson E P, Leiting B, Ruel R, Nicholson D W, Thornberry N A. Inhibition of human caspases by peptide-based and macromolecular inhibitors. *The Journal of biological chemistry* 1998; 273:32608-32613.

40 Castedo M, Perfettini J L, Roumier T et al. The cell cycle checkpoint kinase Chk2 is a negative regulator of mitotic catastrophe. *Oncogene* 2004; 23:4353-4361.

41 Miao E A, Leaf I A, Treuting P M et al. Caspase-1-induced pyroptosis is an innate immune effector mechanism against intracellular bacteria. *Nature immunology* 2010; 11:1136-1142.

42 Degterev A, Huang Z, Boyce M et al. Chemical inhibitor of nonapoptotic cell death with therapeutic potential for ischemic brain injury. *Nature chemical biology* 2005; 1:112-119.

43 Yamamoto A, Tagawa Y, Yoshimori T, Moriyama Y, Masaki R, Tashiro Y. Bafilomycin A1 prevents maturation of autophagic vacuoles by inhibiting fusion between autophagosomes and lysosomes in rat hepatoma cell line, H-4-II-E cells. *Cell structure and function* 1998; 23:33-42.

44 Meijer L, Borgne A, Mulner O et al. Biochemical and cellular effects of roscovitine, a potent and selective inhibitor of the cyclin-dependent kinases cdc2, cdk2 and cdk5. *European journal of biochemistry* 1997; 243:527-536.

45 Lowe S W, Schmitt E M, Smith S W, Osborne B A, Jacks T. p53 is required for radiation-induced apoptosis in mouse thymocytes. *Nature* 1993; 362:847-849.

46 Vakifahmetoglu H, Olsson M, Zhivotovsky B. Death through a tragedy: mitotic catastrophe. *Cell death and differentiation* 2008; 15:1153-1162.

47 Zhang X D, Yang X C, Chung N et al. Robust statistical methods for hit selection in RNA interference high-throughput screening experiments. *Pharmacogenomics* 2006; 7:299-309.

48 Menger L, Vacchelli E, Adjemian S et al. Cardiac glycosides exert anticancer effects by inducing immunogenic cell death. *Science translational medicine* 2012; 4:143ra199.

49 Obeid M, Panaretakis T, Joza N et al. Calreticulin exposure is required for the immunogenicity of gamma-irradiation and UVC light-induced apoptosis. *Cell death and differentiation* 2007; 14:1848-1850.

50 Obeid M, Tesniere A, Ghiringhelli F et al. Calreticulin exposure dictates the immunogenicity of cancer cell death. *Nature medicine* 2007; 13:54-61.

51 Casares N, Pequignot M O, Tesniere A et al. Caspase-dependent immunogenicity of doxorubicin-induced tumor cell death. *The Journal of experimental medicine* 2005; 202:1691-1701.

52 Green D R, Ferguson T, Zitvogel L, Kroemer G. Immunogenic and tolerogenic cell death. *Nat Rev Immunol* 2009; 9:353-363.

The invention claimed is:

1. A method for treating cancer in a subject in need thereof, said method comprising the step of administering to said subject an effective amount of minaprine dihydrochloride.

2. The method according to claim 1, wherein said cancer is brain cancer, gastric cancer, head-and-neck cancer, pancreatic cancer, non-small cell lung cancer, small cell lung cancer, prostate cancer, colon cancer, non-Hodgkin's lymphoma, sarcoma, testicular cancer, acute non-lymphocytic leukemia or breast cancer.

3. The method according to claim 1, wherein said minaprine dihydrochloride is in the form of an injectable pharmaceutical composition.

4. The method according to claim 3, wherein said administering step comprises systemic administration.

5. The method according to claim 3, wherein said administering step comprises intra-tumoral administration.

6. The method according to claim 1, wherein the cancer is gastric cancer, pancreatic cancer, prostate cancer, colon cancer, testicular cancer, and breast cancer.

7. The method according to claim 3, wherein the cancer is brain cancer, head-and-neck cancer, non-small cell lung cancer, small cell lung cancer, non-Hodgkin's lymphoma, sarcoma, and acute non-lymphocytic leukemia.

* * * * *